(12) United States Patent
Li et al.

(10) Patent No.: US 9,249,193 B2
(45) Date of Patent: Feb. 2, 2016

(54) TRUNCATED L1 PROTEIN OF HUMAN PAPILLOMAVIRUS TYPE 33

(75) Inventors: Shaowei Li, Xiamen (CN); Xianglin Kong, Xiamen (CN); Minxi Wei, Xiamen (CN); Huirong Pan, Xiamen (CN); Jun Zhang, Xiamen (CN); Ningshao Xia, Xiamen (CN)

(73) Assignees: Xiamen University, Fujian (CN); Xiamen Innovax Biotech Co. Ltd., Fujian (CN)

( * ) Notice: Subject to any disclaimer, the term of this patent is extended or adjusted under 35 U.S.C. 154(b) by 0 days.

(21) Appl. No.: 14/122,150

(22) PCT Filed: May 22, 2012

(86) PCT No.: PCT/CN2012/075865
§ 371 (c)(1),
(2), (4) Date: Feb. 4, 2014

(87) PCT Pub. No.: WO2012/159562
PCT Pub. Date: Nov. 29, 2012

(65) Prior Publication Data
US 2014/0147460 A1 May 29, 2014

(30) Foreign Application Priority Data

May 25, 2011 (CN) .......................... 2011 1 0136560

(51) Int. Cl.
*A61K 39/12* (2006.01)
*C07K 14/005* (2006.01)
*A61K 39/00* (2006.01)

(52) U.S. Cl.
CPC ............. *C07K 14/005* (2013.01); *A61K 39/12* (2013.01); *A61K 2039/5258* (2013.01); *A61K 2039/55566* (2013.01); *C12N 2710/20022* (2013.01); *C12N 2710/20023* (2013.01); *C12N 2710/20034* (2013.01)

(58) Field of Classification Search
None
See application file for complete search history.

(56) References Cited

FOREIGN PATENT DOCUMENTS

| CN | 1478790 | A | 3/2004 |
|---|---|---|---|
| CN | 101293918 | A | 10/2008 |
| CN | 101343314 | A | 1/2009 |
| CN | 101343315 | A | 1/2009 |
| CN | 101570571 | A | 11/2009 |
| CN | 102229660 | A | 11/2011 |
| WO | 0054730 | A2 | 9/2000 |
| WO | 2008112125 | A1 | 9/2008 |
| WO | 2010012780 | A1 | 2/2010 |

OTHER PUBLICATIONS

GenBank: ACV84012.1. major capsid protein L1 [Human papillomavirus type 33]. http://www.ncbi.nlm.nih.gov/protein/258618453. Sep. 22, 2009.*
Fey et al. Demonstration of in vitron synthesis of human papillomavirusal proteins from hand and foot warts. J. Invest. Dermatol. 1989, 92:817-824.*
Roth et al. Characterization of neutralizing epitopes within the major capsid protein of human papillomavirus type 33. Virol J. Oct. 2, 2006;3:83.*
Chen et al. Papillomavirus Capsid Protein Expression in *Escherichia coli*: Purification and Assembly of HPV11 and HPV16 L1. J. Mol. Biol. (2001) 307, 173-182.*
International Search Report mailed Aug. 9, 2012 (PCT/CN2012/075865); ISA/CN.
EMBL Database, accession No. P06416, Jan. 1, 1988.
Jan. 12, 2015—(EP) Supplemental Extended Search Report—App 12788749.
Ma et al., "Increasing the expression levels of papillomavirus major capsid protein in *Escherichia coli* by N-terminal deletion", Protein Expression and Purification, Academic Press, San Diego, CA vol. 56, No. 1, Oct. 3, 2007, pp. 72-79.
Chen et al., Papillomavirus Capsid protein expression in *Escherichia coli*: purification and assembly of HPV11 and HPV16 L1:, Journal of Molecular Biology, vol. 307, No. 1, Mar. 16, 2001, pp. 173-182.
Cole et al.,: "Genome Organization and Nucleotide Sequence of Human Papillomavirustype 33, Which is Associated With Cervical Cancer", Journal of Virology,vol. 58, No. 3, Jun. 1, 1986, pp. 991-995.

* cited by examiner

*Primary Examiner* — Stacy B Chen
*Assistant Examiner* — Nick Zou
(74) *Attorney, Agent, or Firm* — Banner & Witcoff, Ltd.

(57) ABSTRACT

The present invention relates to a truncated L1 protein of Human Papillomavirus (HPV) Type 33, a sequence encoding the same, a method for preparing the same, and a virus-like particle comprising the same, wherein the protein and the virus-like particle are useful for preventing HPV (particularly HPV33) infection, and a disease caused by HPV (particularly HPV33) infection, such as cervical cancer. The invention also relates to the use of the protein and the virus-like particle in the preparation of a pharmaceutical composition or a vaccine for preventing HPV (particularly HPV33) infection, and a disease caused by HPV (particularly HPV33) infection, such as cervical cancer.

19 Claims, 6 Drawing Sheets

TRUNCATED L1 PROTEIN OF HUMAN PAPILLOMAVIRUS TYPE 33

The present application is a U.S. National Phase Entry of PCT/CN2012/075865, filed on May 22, 2012, designating the United States of America and claiming priority to Chinese Patent Application No. 201110136560.6, filed May 25, 2011. The present application claims priority to and the benefit of all the above-identified applications, and all the above-identified applications are incorporated by reference herein in their entireties.

This application incorporates by reference the contents of a 31.0 kb text file created on Nov. 25, 2013, and named "sequencelisting.txt," which is the sequence listing for this application.

FIELD OF THE INVENTION

The invention relates to the field of molecular virology and immunology. In particular, the invention relates to a truncated L1 protein of Human Papillomavirus (HPV) Type 33, a sequence encoding the same, a method for preparing the same, and a virus-like particle comprising the same, wherein the protein and the virus-like particle are useful for preventing HPV (particularly HPV33) infection, and a disease caused by HPV (particularly HPV33) infection, such as cervical cancer. The invention also relates to the use of the protein and the virus-like particle in the preparation of a pharmaceutical composition or a vaccine for preventing HPV (particularly HPV33) infection, and a disease caused by HPV (particularly HPV33) infection, such as cervical cancer.

BACKGROUND OF THE INVENTION

Human Papillomavirus (HPV), a non-enveloped, deoxyribonucleic acid (DNA) virus, belongs to the family Papillomaviridae. The viral genome is a double-stranded, closed circular DNA, which is of approximately 7.2-8 kb in length and contains 8 open reading frames (ORFs). The genome can be divided into three parts in terms of function: (1) the early region (E), approximately 4.5 Kb in length, coding for 6 non-structural proteins E1, E2, E4~E7 associated with virus replication, transcription and transformation; (2) the late region (L), approximately 2.5 Kb in length, coding for the major capsid protein L1 and the minor capsid protein L2; (3) the long control region (LCR), located between the end of the L region and the initiating terminal of the E region, approximately 800-900 bp in length, and comprising regulator elements for DNA replication and expression instead of coding for proteins. HPV viral particles have a diameter of 45-55 nm, wherein the nucleocapsid, consisting of L1 and L2, exhibits icosahedral symmetry and comprises 72 capsomers.

Currently, there are over 90 different types of HPV, mainly causing papillary disease in the skin and mucosa of human. HPV types are divided into three groups depending on their relation with tumorigenesis: (1) group of low or no cancerogenic risk, containing HPV 6, 11, 39, 41, 42, and 43; (2) group of medium cancerogenic risk, containing HPV 31, 33, 35, 51 and 52; and (3) group of high cancerogenic risk, containing HPV 16, 18, 58 and 45.

HPV molecular epidemiological investigation demonstrates that infection by high-risk HPV types is an important factor responsible for the development of cervical cancer. Among all the cervical cancer specimens, HPV DNA is detected in over 80% of them. Cervical cancer is a common malignant tumor among women, the incidence of which is only next to breast cancer, and seriously threatens the health of women. There are about 490,000 newly reported cases worldwide every year, and nearly 270,000 people die of this disease annually (Boyle, P., and J. Ferlay. Ann Oncol 2005, 16:481-8). Cases in developing countries account for approximately 83% of the total cervical cancer cases. In these developing countries, the cervical cancer cases account for about 15% of female malignant tumors, in contrast to 1.5% in developed countries. Cervical cancer is most prevalent in sub-Saharan Africa, central and Southern Asia, Latin America, and Eastern Asia. Cervical cancer is also prevalent in China. The incidence of cervical cancer among married women is as high as 1026/100000 in Lueyang County of Shanxi Province.

Meta-analysis of the distribution of HPV types in the worldwide cervical cancer specimens shows that the most common HPV types found in cervical cancer specimens are HPV 16, 18, 45, 31, 33, 58, 52, 35, 59, 56, 6, 51, 68, 39, 82, 73, 66 and 70 (listed in a descending order, Clifford G M, Smith J S, Plummer M, et al. Br J Cancer, 2003, 88(1): 63-73). Recently, an investigation on the HPV types infected in Chinese women shows that in cervical cancer patients, the infection rate of HPV33 is 3.6%, preceded only by HPV16 (58.7%), HPV18 (11.0%), and HPV58 (7.2%), and ranked 4th (Y P Bao, N Li, J S Smith and Y L Qiao. International Journal of STD & AIDS, 2008, 19: 106-111). This suggests that HPV33 has a high infection rate in women with cervical cancer worldwide and is one of the commonly susceptible HPV types.

Currently, the commercially available HPV vaccines are Gardasil® from Merck and Cervarix® from GSK, which comprise HPV6/11/16/18 VLPs and HPV16/18 VLPs, respectively, but do not comprise VLPs of HPV type 33 which is commonly susceptible to women in China and Asia.

Therefore, HPV vaccines which are safe and effective for women in developing countries such as in China and Asia, in particular, those directed to high-risk type such as HPV 16, 18 and 33, are effective means for effectively preventing cervical cancer and improving the health condition of women, in particular women in China and Asia.

HPV L1 protein, with a molecular weight of 55-60 kDa, is the major capsid protein of the human papillomavirus and the main target protein of the HPV vaccine. HPV L1 protein expressed in many expression systems can form Virus-Like Particles (VLPs) which resemble native HPV particles morphologically, without the assistance of the L2 protein. The VLPs, consisting of 72 pentamers of the L1 proteins, exhibit icosahedral symmetry. Since the VLPs retain the native epitopes of the viral particles, they are highly immunogenic and can induce the generation of neutralization antibodies against homologous HPV (Kirnbauer, R., F. Booy, et al. 1992 Proc Natl Acad Sci USA 89(24): 12180-4). Furthermore, the VLPs are safe and have no potential cancergenic risk as they contain no viral nucleic acids. Therefore, VLP vaccines have become the primary candidate for HPV vaccines.

The key for development of HPV VLP vaccines lies in efficient production of VLP samples in large-scale. Currently, the most common expression systems used for VLP are divided into eukaryotic expression systems and prokaryotic expression systems.

The commonly used eukaryotic expression systems comprise poxvirus, insect baculovirus and yeast expression systems. HPV L1 protein expressed in eukaryotic expression systems shows little conformational difference from that of the native virus, and can self-assemble into VLPs. Thus, purified VLPs can be easily obtained after simple gradient density centrifugation. It brings a lot of convenience to the purification work. However, due to the high culture costs and low expression level of eukaryotic expression systems, it is quite difficult to product industrially on a large-scale. The HPV vaccine Gardasil®, which came into the market recently, is more expensive than others due to low expression level and high production cost of the *Saccharomyces cerevisiae* expression system employed in its manufacture, and therefore, its general application is limited.

The expression of HPV L1 protein in a prokaryotic expression system such as *E. coli* expression system has been previously reported. The expression of HPV 16 L1 protein by employing *E. coli* has been reported (Banks, L., G. Matlashewski, et al. (1987). J Gen Virol 68 (Pt 12): 3081-9). However, most HPV L1 proteins expressed in *E. coli* lose their native conformation and cannot induce protective antibodies against HPV. Alternatively, although HPV VLPs can be obtained from the proteins by steps such as purification from inclusion bodies and renaturation (Kelsall, S. R. and J. K. Kulski (1995). J Virol Methods 53(1): 75-90), it is difficult to apply this method to large-scale production, as the proteins are largely lost during the renaturation process and the yield is low. Although HPV L1 protein may be expressed in a soluble form with a correct conformation in *E. coli* and be dissolved in the supernatants of *E. coli* lysate, the expression level is low. Moreover, since there are large number and amounts of impure proteins, it is difficult to isolate the proteins of interest from them. Although it is also reported that the expression level of L1 protein can be increased in the supernatants by means of GST fusion expression and the purification of the protein of interest is facilitated (Li, M., T. P. Cripe, et al. (1997), J Virol 71(4): 2988-95), it still cannot be applied to larger-scale production because expensive enzymes are required to cleave the fusion protein.

Therefore, the obtainment of a HPV L1 protein capable of inducing the generation of protective antibodies against HPV, and a virus-like particle consisting of the same, at low cost, are still urgent in the art, so as to make the large-scale industrial production of vaccines for cervical cancer possible.

DESCRIPTION OF THE INVENTION

The invention is at least partially based on the inventors' surprised discovery: a truncated HPV33 L1 protein capable of inducing the generation of neutralization antibodies against HPV33 can be expressed in an *E. coli* expression system on a large scale, wherein the truncated HPV33 L1 protein can be produced with a high yield, and the purity of the purified protein reaches at least 96% or higher; and moreover, further treatment of the purified protein results in the obtainment of VLPs capable of inducing the generation of protective antibodies against HPV33.

Therefore, in one aspect, the invention relates to a truncated HPV33 L1 protein or variants thereof, wherein said protein has 9-19 amino acids, for example, 9, 10, 11, 12, 13, 14, 15, 16, 17, 18 and 19 amino acids, truncated at its N-terminal, as compared with wild type HPV33 L1 protein.

In a preferred embodiment, the truncated HPV33 L1 protein has 9, 11, 14 or 19 amino acids, truncated at its N-terminal, as compared with wild type HPV33 L1 protein.

In another preferred embodiment, the truncated HPV33 L1 protein (referred to hereafter as the truncated protein) has an amino acid sequence as set forth in SEQ ID NO: 4, SEQ ID NO: 5, SEQ ID NO: 6, or SEQ ID NO: 7. In another preferred embodiment, the truncated protein has an amino acid sequence as set forth in SEQ ID NO: 4.

In another aspect, the invention relates to a polynucleotide encoding the truncated protein or variants thereof according to the invention, and a vector containing the polynucleotide.

Vectors useful for insertion of a polynucleotide of interest are well known in the art, including, but not limited to clone vectors and expression vectors. In one embodiment, the vectors are, for example, plasmids, phages, cosmids, etc.

In another aspect, the invention also relates to a host cell comprising the polynucleotide or vector as described above. The host cell includes, but is not limited to prokaryotic cells such as *E. coli* cells, and eukaryotic cells such as yeast cells, insect cells, plant cells and animal cells (such as mammalian cells, for example, mouse cells, human cells, etc.). The host cell according to the invention may also be a cell line, such as 293T cell.

In another aspect, the invention relates to a HPV33 virus-like particle, comprising or consisting of or formed from the truncated protein or variants thereof according to the invention.

In one preferred embodiment, the HPV33 virus-like particle according to invention comprises or is consisted of or formed from the truncated HPV33 L1 protein having 9-19 amino acids, for example, 9, 11, 14, or 19 amino acids, truncated at its N-terminal, as compared with wild type HPV33 L1 protein. In a particularly preferred embodiment, the HPV33 virus-like particle according to invention comprises or is consisted of or formed from the truncated HPV33 L1 protein having a sequence as set forth in SEQ ID NO: 4, 5, 6, or 7.

In another aspect, the invention also relates to a composition comprising said truncated protein or variants thereof, or said polynucleotide or vector or host cell or HPV33 virus-like particle. In one preferred embodiment, the composition comprises the truncated protein or variants thereof according to the invention. In another preferred embodiment, the composition comprises the HPV33 virus-like particle according to the invention.

In another aspect, the invention also relates to a pharmaceutical composition or vaccine comprising the HPV33 virus-like particle according to invention, and optionally pharmaceutically acceptable carriers and/or excipients. The pharmaceutical composition or vaccine according to the invention is useful for preventing HPV (particularly HPV33) infection, and a disease caused by HPV (particularly HPV33) infection, such as cervical cancer.

In one preferred embodiment, the HPV33 virus-like particle is present in an amount effective for preventing HPV infection or cervical cancer. In another preferred embodiment, the pharmaceutical composition or vaccine according to the invention further comprises at least one virus-like particle selected from the group consisting of HPV6 L1 protein virus-like particle, HPV11 L1 protein virus-like particle, HPV16 L1 protein virus-like particle, HPV18 L1 protein virus-like particle, HPV31 L1 protein virus-like particle, HPV45 L1 protein virus-like particle, HPV52 L1 protein virus-like particle, and HPV58 L1 protein virus-like particle; preferably these virus-like particles are independently present in an amount effective for preventing cervical cancer or infection by the corresponding HPV subtype.

The pharmaceutical composition or vaccine according to the invention may be administrated by methods well known in the art, for example, but not limited to, orally or by injection. In the invention, the particularly preferred administration route is injection.

In one preferred embodiment, the pharmaceutical composition or vaccine according to the invention is administrated in a form of a unit dosage. For example, but not for limiting the invention, each unit dosage contains 5 μg-80 μg, preferably 20 μg-40 μg HPV33 virus-like particle.

In another aspect, the invention relates to a method for obtaining the truncated protein according to the invention, comprising expressing the truncated protein according to the invention with an *E. coli* expression system, and carrying out a purification treatment on the lysed supernatant containing the truncated protein, In a preferred embodiment, the method for obtaining the truncated protein according to the invention comprises a) expressing the truncated protein in *E. coli*;

b) disrupting the *E. coli*, which has expressed the truncated protein, in a solution with a salt concentration of 100 mM to 600 mM, and isolating the supernatant;

c) decreasing the salt concentration of the supernatant obtained in step b) to 100 mM or less, by using water or a solution at a low salt concentration, lowest to 0, and collecting a precipitate;

d) re-dissolving the precipitate of c) in a solution with a salt concentration of 150 mM to 2500 mM and adding a reductant to the solution, and then isolating the resultant solution, wherein the resultant solution contains the truncated HPV33 L1 protein with a purity of at least 50%.

More generally, the invention also relates to a method for obtaining HPV L1 protein such as the truncated protein according to the invention, comprising:

a) expressing HPV L1 gene encoding HPV L1 protein in *E. coli*;

b) disrupting the *E. coli*, which has expressed the HPV L1 protein, in a solution with a salt concentration of 100 mM to 600 mM, and isolating the supernatant;

c) decreasing the salt concentration of the supernatant obtained in step b) to 100 mM or less, by using water or a solution at a low salt concentration, lowest to 0, and collecting a precipitate;

d) re-dissolving the precipitate of c) in a solution with a salt concentration of 150 mM to 2500 mM and adding a reductant to the solution, and then isolating the resultant solution, wherein the resultant solution contains the HPV L1 protein with a purity of at least 50%.

The invention also relates to a method for obtaining the HPV33 virus-like particle according to invention, on the basis of the obtainment of the truncated protein of the invention, comprising the steps of:

e) further purifying the truncated HPV33 L1 protein with a purity of at least 50% by a chromatography; and f) removing the reductant from the truncated protein obtained in e).

The invention also relates to a method for preparing a vaccine, comprising blending the HPV33 virus-like particle according to the invention, and optionally, one or more virus-like particles selected from the group consisting of virus-like particles of HPV types 6, 11, 16, 18, 31, 45, 52 and 58, with pharmaceutically acceptable carriers and/or excipients. As described above, the vaccine obtained is useful for preventing HPV (particularly HPV33) infection, and a disease caused by HPV (particularly HPV33) infection, such as cervical cancer.

In another aspect, the invention relates to a method for preventing HPV infection or a disease caused by HPV infection, comprising administrating a prophylactically effective amount of the HPV33 virus-like particle or pharmaceutical composition or vaccine according to the invention. In one preferred embodiment, the HPV infection is HPV33 infection. In another preferred embodiment, the disease caused by HPV infection includes, but is not limited to cervical cancer. In another preferred embodiment, the subject is mammalian, such as human.

In another aspect, the invention also relates to the use of the truncated protein or the HPV33 virus-like particle according to invention in the preparation of a pharmaceutical composition or vaccine for preventing HPV infection or a disease caused by HPV infection. In one preferred embodiment, the HPV infection is HPV33 infection. In another preferred embodiment, the disease caused by HPV infection includes, but is not limited to cervical cancer.

DEFINITIONS OF THE TERM IN PRESENT INVENTION

In the invention, unless otherwise specified, the scientific and technical terms used herein have the meanings as generally understood by a person skilled in the art. Moreover, the laboratory operations of cell culture, molecular genetics, nucleic acid chemistry, and immunology used herein are the routine operations widely used in the corresponding fields. Meanwhile, in order to better understand the invention, the definitions and explanations of the relevant terms are provided as follows.

According to the invention, the term "a protein having X amino acids truncated at its N-terminal" refers to a protein resulted from substitution of the amino acid residues from positions 1 to X at the N-terminal of the protein with methionine residue encoded by an initiator codon (for initiating protein translation). For example, a HPV33 L1 protein having 9 amino acids truncated at its N-terminal refers to a protein resulted from substituting the amino acid residues from positions 1 to 9 at the N-terminal of wild type HPV33 L1 protein with methionine residue encoded by an initiator codon.

According to the invention, the term "variant" refers to a protein, whose amino acid sequence is different from the truncated HPV33 L1 protein according to the invention (for example, the protein as set forth in SEQ ID NO: 4, 5, 6 or 7) by one or more (for example, 1-10, or 1-5 or 1-3) amino acids, or which has an identity of at least 60%, 80%, 85%, 90%, 95%, 96%, 97%, 98%, or 99% to the truncated HPV33 L1 protein according to the invention (for example, the protein as set forth in SEQ ID NO: 4, 5, 6 or 7), and which retains the essential characteristics of the truncated protein. The term "essential characteristics" may be one or more of the following characteristics: capable of inducing the generation of neutralization antibodies against HPV33; capable of being expressed in *E. coli* in a soluble manner; capable of obtaining purified protein with a high yield by the expression and purification methods as involved in the invention. The term "identity" refers to the similarity degree of nucleotide sequences or amino acid sequences. Generally, sequences were aligned to obtain a maximum matching. "Identity" has well-known meanings in the art and can be calculated by published algorithm (such as BLAST).

According to the invention, the term "*E. coli* expression system" refers to an expression system consisting of *E. coli* (strain) and a vector, wherein the *E. coli* (strain) includes, but are not limited to: ER2566, BL21 (DE3), B834 (DE3), and BLR (DE3), which are available on the market.

According to the invention, the term "vector" refers to a nucleic acid vehicle which can have a polynucleotide inserted therein. When the vector allows for the expression of the protein encoded by the polynucleotide inserted therein, the vector is called an expression vector. The vector can have the carried genetic material elements expressed in a host cell by transformation, transduction, and transfection into the host cell. Vectors are well known by a person skilled in the art, including, but not limited to plasmids, phages, cosmids and the like.

According to the invention, the term "a truncated HPV33 L1 protein" refers to the protein having one or more amino acids deleted at the N- and/or C-terminal of wild-type HPV33 L1 protein, wherein the example of the wild-type HPV33 L1 protein includes, but is not limited to, the full-length L1 proteins such as P06416.1, ACV84008.1, ACV84011.1, ACV84012.1 or ACL12333.1 in NCBI database.

The term "a gene fragment of a truncated HPV33 L1 protein" refers to the gene fragments having the nucleotide(s) encoding one or more amino acids deleted at 5' or 3' terminal of the wild-type HPV33 L1 gene (cDNA), wherein the full-length gene sequence of the wild-type HPV33 L1 gene includes, but is not limited to, the following sequences: GQ479013.1, GQ479014.1, M12732.1, GQ479012.1, GQ479015.1, GQ479016.1, EU918766.1, GQ479017.1, GQ479018.1 or GQ479019.1, etc. in NCBI database.

According to the invention, the term "pharmaceutically acceptable carriers and/or excipients" refers to carriers and/or excipients that are pharmacologically and/or physiologically compatible with subjects and active ingredients, and are well known in the art (see, for example, Remington's Pharmaceutical Sciences. Edited by Gennaro A R, 19th ed. Pennsylvania: Mack Publishing Company, 1995), including, but not limited to pH adjusting agents, surfactants, adjuvants, and ionic strength enhancers. For example, pH adjusting agents include, but are not limited to, phosphate buffers; surfactants include, but are not limited to: anion surfactants, cation surfactants, or non-ionic surfactants (for example, Tween-80); adjuvants include, but are not limited to, aluminum adjuvants (for example, aluminum hydroxide) and Freund's adjuvants (for example, Freund's complete adjuvant); and ionic strength enhancers include, but are not limited to, NaCl.

According to the invention, the term "an effective amount" refers to an amount that can effectively achieve the intended purpose. For example, an amount effective for preventing a disease (such as HPV infection) refers to an amount effective for preventing, suppressing, or delaying the occurrence of a disease (such as HPV infection). The determination of such an effective amount is within the ability of a person skilled in the art.

According to the invention, the term "chromatography" includes, but is not limited to: ion exchange chromatography (e.g. cation-exchange chromatography), hydrophobic interaction chromatography, absorbent chromatography (e.g. hydroxyapatite chromatography), gel filtration chromatography (gel exclusion chromatography), and affinity chromatography.

According to the invention, the truncated HPV33 L1 proteins according to the invention may be obtained preferably by the following steps:

disrupting *E. coli*, which expresses a truncated HPV33 L1 protein, in a buffer at a salt concentration of 100-600 mM, preferably 200-500 mM, and centrifuging the disrupted solution to obtain a supernatant;

precipitating the truncated HPV33 L1 protein from the supernatant by decreasing the salt concentration of the resultant supernatant to 100 mM-0 mM with water or a low-salt solution (generally, with a salt concentration lower than the one of the buffer for disrupting);

re-dissolving the precipitate in a solution containing a reductant and having a salt concentration of 150-2500 mM, preferably greater than 200 mM, resulting in a solution comprising the truncated HPV33 L1 proteins with a purity of at least 50%, preferably at least 70%, more preferably at least 80%.

The buffers used in the methods of the invention are well known in the art, including, but not limited to Tris buffers, phosphate buffers, HEPES buffers, MOPS buffers, etc.

According to the invention, the disrupting of the host cell can be accomplished by methods well known by a person skilled in the art, including, but not limited to homogenizer disrupting, ultrasonic treatment, grinding, high pressure extrusion, lysozyme treatment, etc.

The salts used in the methods of the invention include, but are not limited to: one or more of acidic salts, basic salts, neutral salts, for example, alkali metal salts, alkaline-earth metal salts, ammonium salts, hydrochlorides, sulfates, bicarbonates, phosphate salts or biphosphates, especially NaCl, KCl, $NH_4Cl$, $(NH_4)_2SO_4$. NaCl is particularly preferred. The reductant used in the methods of the invention includes, but is not limited to, DTT and 2-mercaptoethanol, in an amount including, but not limited to, 10-100 mM.

According to the invention, the HPV33 VLPs according to the invention may be produced by the following steps: further purifying the truncated HPV33 L1 protein with a purity of at least 50% as described above by e.g. a chromatography, and thereby obtaining a purified truncated protein solution; and removing the reductant from the solution to obtain the HPV33 VLPs. Methods for removing the reductant are known in the art, including, but not limited to, dialysis, ultrafiltration, and chromatography.

Beneficial Effect

Presently, the expression systems useful for preparing HPV VLPs include eukaryotic and prokaryotic expression systems.

HPV L1 proteins expressed in eukaryotic expression systems show little conformational difference from that of the native virus, and can self-assemble into VLPs. In most cases, VLPs with a correct conformation can be obtained by simple purification. Nevertheless, eukaryotic expression systems, such as the baculovirus and yeast expression systems, are difficult to be applied to large-scale industrial production due to shortcomings such as low expression levels and high culturing costs.

Prokaryotic expression systems, such as *E. coli* systems, have the advantages of high expression levels and low culturing costs. However, when expressed in *E. coli* system, HPV L1 proteins usually lose their native conformations and are expressed in a form of inclusion bodies in the precipitant. Currently, renaturation of the protein from inclusion bodies is still a challenge worldwide. Due to the difficulty and inefficiency of renaturation, this method is limited to small-scale lab research and cannot be applied to the large-scale obtainment of VLPs with a correct conformation from the inclusive bodies. Although HPV L1 protein may be expressed in a soluble form with a correct conformation in *E. coli*, their expression levels are low. Moreover, it is quite difficult to purify the HPV L1 proteins from the numerous soluble proteins in the *E. coli* lysate supernatant. Generally, the purification is carried out by means such as fusion expression and affinity chromatography which are not feasible for industrial-scale processes due to expensive enzymes employed therein.

The N-truncated HPV33 L1 protein and the method for preparing the same, as provided in the invention, effectively solve the problem. Firstly, *E. coli* expression systems are used in the invention to express the N-truncated HPV33 L1 protein, which ensures a high expression level. Secondly, the truncated protein is selectively precipitated from the *E. coli* lysate supernatant under mild conditions. The truncated protein is then redissolved in a salt buffer to significantly improve its purity while still retaining its correct conformation. The truncated protein solution thus obtained can be further purified directly by chromatography such as ion-exchange and hydrophobic exchange chromatography so as to obtain the protein of interest with a high purity (such as a purity up to 96%). Further, the purified, truncated protein obtained from these steps, can self-assemble into VLP with good immunogenicity and the ability to induce neutralization antibodies of a high titer against HPV33, which is a good vaccine for preventing HPV33 infection in human.

Therefore, the invention has the following advantages. The truncated protein of the invention can be expressed in *E. coli* expression systems on a large scale whilst retaining the antigenicity and particle self-assembly ability of the full-length HPV33 L1 protein. Expensive enzymes are not required in the preparation methods used in the invention, i.e. the cost is low. Furthermore, since the truncated protein is not subjected to the intensive procedures of denaturation and renaturation during purification, the loss of the protein is low and the yield is high. The VLPs formed from the truncated protein can induce the generation of protective antibodies against HPV at a high titer and can be applied to the preparation of vaccines. Thus, the truncated protein of the invention and the preparation method thereof can be applied to large-scale industrial production, and makes the large-scale industrial production of vaccines for cervical cancer possible.

The embodiments of the invention are further described in detail by reference to the drawings and examples. However, a person skilled in the art would understand that the following drawings and examples are intended for illustrating the invention only, rather than defining the scope of the invention. According to the detailed description of the following drawings and preferred embodiments, various purposes and advantages of the invention are apparent for a person skilled in the art.

SPECIFIC MODES FOR CARRYING OUT THE INVENTION

Figure 1:
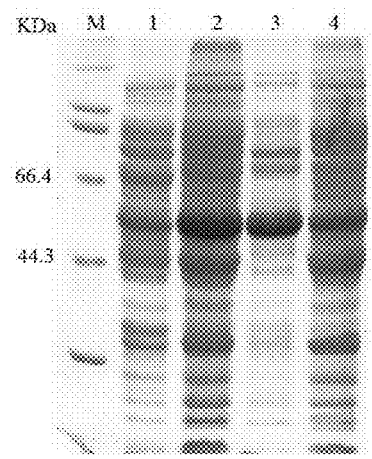
FIG. 1 shows the SDS-PAGE result of the HPV33N9C-L1 protein obtained during different steps of Example 2 of the invention. Lane M: protein molecular weight marker; Lane 1: supernatant of disrupted bacteria (i.e. the supernatant obtained by centrifuging the disrupted bacteria); Lane 2: precipitate product free of salts (i.e. the precipitate obtained by centrifugation after dialysis); Lane 3: re-dissolved supernatant (i.e. the supernatant obtained by centrifuging the solution resulted from re-dissolving the precipitate product free of salts); Lane 4: precipitant obtained after re-dissolution (i.e. the precipitate obtained by centrifuging the solution resulted from re-dissolving the precipitate product free of salts). The result showed that the purity of HPV33N9C-L1 protein was increased from about 10% to about 70% (see Lane 1 and 3) after the steps of precipitation and re-dissolution.

The present invention is further illustrated in detail by reference to the examples as follows. It is understood by those skilled in the art that the examples are used only for the purpose of illustrating the present invention, rather than limiting the protection scope of the present invention.

Unless indicated otherwise, the molecular biological experimental methods and immunological assays used in the present invention are carried out substantially in accordance with the methods as described in Sambrook J et al., Molecular Cloning: A Laboratory Manual (Second Edition), Cold Spring Harbor Laboratory Press, 1989, and F. M. Ausubel et al., Short Protocols in Molecular Biology, 3$^{rd}$ Edition, John Wiley & Sons, Inc., 1995; and restriction enzymes are used under the conditions recommended by the manufacturers. Those skilled in the art understand that the examples are used for illustrating the present invention, but not intended to limit the protection scope of the present invention.

Example 1

Expression of the Truncated HPV33 L1 Protein Set Forth in SEQ ID NO: 4

Preparation of HPV33 L1 Full-Length Gene Fragment

The DNA, extracted from the vaginal secretion of patients with cervical cancer from Xiamen City, Fujian Province, was used as template. The forward primer was HPV33S: 5'-CAT ATG TCC GTG TGG CGG CCT AG-3' (SEQ ID NO:12), and the reverse primer was HPV33 R: 5'-GTC GAC TTA TTT TTT AAC CTT TTT GC-3' (SEQ ID NO:13). The PCR reaction was performed in a PCR thermocycler (Biometra T3) to prepare HPV33 L1 full-length gene fragment under the following conditions:

| | |
|---|---|
| 94° C. denaturation 10 min | 1 cycle |
| 94° C. denaturation 50 sec | 25 cycles |
| 56° C. annealing 50 sec | |
| 72° C. elongation 1.5 min | |
| 72° C. elongation 10 min | 1 cycle |

In HPV33-positive samples, the products of about 1.5 kb in length were obtained after amplification. After sequencing, three HPV33 L1 gene sequences (SEQ ID NOs: 1, 2 and 3) were obtained. In the present Example, SEQ ID NO: 1 was used as template for preparing the DNA fragment encoding the truncated protein of the present invention.

Construction of Non-Fusion Expression Vectors for the Truncated HPV33 L1 Proteins The full-length HPV33 L1 gene fragment (SEQ ID NO: 1) obtained in the last step was used as template. The forward primer was HPV33N9F: 5'-CAT ATg ACA gTg TAC CTg CCT CCT-3' (SEQ ID NO: 14), at the 5' terminal of which the restriction endonuclease NdeI site CAT ATG was introduced, wherein ATG was the initiation codon in E. coli system. The reverse primer was HPV33R: 5'-GTC GAC TTA TTT TTT AAC CTT TTT GC-3' (SEQ ID NO: 13), at the 5' terminal of which the restriction endonuclease SalI site was introduced. The PCR reaction was performed in a PCR thermocycler (Biometra T3) under the following conditions:

| | |
|---|---|
| 94° C. denaturation 10 min | 1 cycle |
| 94° C. denaturation 50 sec | 25 cycles |
| 56° C. annealing 50 sec | |
| 72° C. elongation 1.5 min | |
| 72° C. elongation 10 min | 1 cycle |

The DNA fragments, about 1.5 kb in length, were obtained after amplification. The PCR products were linked into the commercially available pMD 18-T vector (produced by Takara Co.), and were transformed into E. coli. Positive bacterial colonies were screened, and plasmids were extracted. After digestion with NdeI/SalI, it was identified that positive clones, designated as pMD 18-T-HPV33N9C-L1, were obtained, wherein the truncated HPV33 L1 gene was inserted.

The nucleotide sequence of the fragment of interest, which was inserted into the plasmid pMD 18-T-HPV33N9C-L1, was determined as SEQ ID NO: 8 using M13 (+)/(−) primers, and the amino acid sequence encoded thereby was set forth in SEQ ID NO: 4. The sequence corresponded to a HPV33 L1 protein having 9 amino acids truncated at its N-terminal and no amino acid truncated at its C-terminal, designated as HPV33N9C-L1.

The HPV33N9C-L1 gene fragment was obtained by NdeI/SalI digestion of plasmid pMD 18-T-HPV33N9C-L1. The fragment was linked into the prokaryotic expression vector pTO-T7 (Luo Wenxin et al., Chinese Journal of Biotechnology, 2000, 16:53-57) digested with NdeI/SalI, and was transformed into ER2566 bacteria. Plasmids were extracted. After digestion with NdeI/SalI, it was identified that positive clones, designated as pTO-T7-HPV33N9C-L1, were obtained, wherein the fragment of interest was inserted.

1 μL plasmid pTO-T7-HPV33N9C-L1 (0.15 mg/ml) was used to transform 404 competent E. coli ER2566 (purchased from New England Biolabs) prepared by the Calcium chloride method, and then the bacteria were plated on solid LB medium (the components of the LB medium: 10 g/L peptone, 5 g/L yeast powder, and 10 g/L NaCl, the same as below) containing kanamycin (at a final concentration of 25 mg/ml, the same as below). The plates were statically incubated at 37° C. for about 10-12 h until single colonies could be observed clearly. Single colonies from the plates were transferred to a tube containing 4 ml liquid LB media containing kanamycin. The cultures were incubated in a shaking incubator at 220 rpm for 10 h at 37° C., and then 1 ml bacterial solution was taken and stored at −70° C.

Expression of HPV33N9C-L1 Protein on a Large Scale

The E. coli solution carrying the recombinant plasmid pTO-T7-HPV33N9C-L1 at −70° C. was seeded in 50 mL LB liquid medium containing kanamycin and incubated at 200 rpm and 37° C. for about 8 h. Then, the cultures were transferred to ten flasks (5 ml cultures per flask), each of which contained 500 mL LB medium containing kanamycin, and was incubated in a shaking incubator overnight at 200 rpm and 37° C., as a starter culture.

A 50 L fermenter made by Shanghai Baoxing Biological Ltd was used in large-scale culture. PH electrode of the fermenter was calibrated. 30 L LB medium was loaded into the fermenter, in situ sterilized at 121° C. for 30 minutes. Oxygen-dissolved electrode was calibrated, wherein the value was determined as 0 prior to introduction of air after sterilization and as 100% prior to vaccination after introduction of air while stirring at an initial rate of 100 rpm.

Preparation of the feed: 20 g peptone and 10 g yeast extract were dissolved in 100 mL deionized water to prepare a mixture of peptone and yeast extract solution (30%), and 50 g glucose was dissolved in 100 ml deionized water to prepare a glucose solution (50%). The two solutions were sterilized at 121° C. for 20 min.

On the next day, the starter cultures in the ten flasks (5 L in total) were transferred to the fermenter. A temperature of 37° C. and a pH value of 7.0 were set, the dissolved $O_2$ was maintained at >40% by regulating agitation rate and air supply manually.

Flow Feed: glucose (50%) and a mixture of peptone and yeast (30%) were mixed at a solute mass ratio of 2:1.

Flow rates were as followed (25 ml/min was defined as 100%):

1$^{st}$ h: 5%;
2$^{nd}$ h: 10%;
3$^{rd}$ h: 20%;
4$^{th}$ h: 40%;
5$^{th}$ h to the end: 60%.

When the bacterial concentration reached an OD$_{600}$ of about 10.0, the culturing temperature was lowered to 25° C. and 4 g IPTG was added to initiate an induction culture of 4 h. Fermentation was halted when the final concentration reached an OD$_{600}$ of about 60. The bacteria expressing HPV33N9C-L1 protein were obtained, weighted about 2.5 kg.

Example 2

Preparation of HPV33N9C-L1 Protein with a Purity of about 70%

Bacteria were re-suspended at a proportion of 1 g bacteria to 10 ml lysis buffer (20 mM Tris buffer pH 7.2, 300 mM NaCl). Bacteria were disrupted by an APV homogenizer (Invensys Group) for five times at a pressure of 600 bar. The homogenate was centrifuged at 13,500 rpm (30,000 g) for 15 min, and the supernatant (i.e. the supernatant of disrupted bacteria) was obtained. The supernatant was subjected to 10% SDS-PAGE. At this stage, the HPV33N9C-L1 protein in the supernatant had a purity of about 10% (see FIG. 1, Lane 1).

The supernatant was dialyzed by a CENTRASETTE 5 Tangential Flow Filter (Pall Co.) running at a pressure of 0.5 psi, a flow rate of 500 ml/min, and a tangential flow rate of 200 mL/min, wherein the membrane retention molecular weight was 30 kDa, the dialysis solution was 10 mM phosphate buffer pH 6.0, and the dialysis volume was three times of the volume of the supernatant.

After thorough dialysis, the mixture was centrifuged at 9500 rpm (12,000 g) using Beckman J25 high speed centrifuge for 20 min, and the precipitate (i.e. the precipitate product free of salts) was collected. The precipitate was re-suspended in 20 mM phosphate buffer (pH 8.0) containing 20 mM DTT and 300 mM NaCl, wherein the volume of the buffer was 1/10 of the volume of the supernatant. The mixture was stirred for 30 min and centrifuged at 13,500 rpm (30,000 g) using Beckman J25 high speed centrifuge for 20 min. The supernatant and precipitate (i.e. the precipitate obtained after re-dissolution) were collected. 20 mM phosphate buffer (pH 8.0) containing 20 mM DTT was used to dilute the supernatant to a volume three times of the original one, so that the final concentration of NaCl was 0.1 M. Then, the supernatant passed through a filter membrane with an aperture of 0.22 μm. The sample obtained (i.e. re-dissolved supernatant) was used for the purification with cation exchange chromatography (as described in Example 3). 30 μL of 6× loading buffer (12% (w/v) SDS, 0.6% (w/v) bromophenol blue, 0.3M Tris-HCl pH 6.8, 60% (v/v) glycerin, 5% (v/v) β-mercaptoethanol) was added to 150 μL filtered supernatant, and the resultant solution was mixed homogeneously and was placed in a water bath at 80° C. for 10 min. Then, 10 μl sample was subjected to 10% SDS-PAGE at 120V for 120 min. The electrophoretic bands were stained by Coomassie brilliant blue. The electrophoretic result was shown in FIG. 1. The result showed that HPV33N9C-L1 protein was purified and enriched after the steps of precipitation and re-dissolution, with a purity increased from about 10% to about 70% (see FIG. 1, Lane 1 and Lane 3).

Example 3

Chromatographic Purification of HPV33N9C-L1 Protein

Purification of HPV33N9C-L1 by Cation Exchange Chromatography

Equipment: AKTA Explorer 100 preparative liquid chromatography system produced by GE Healthcare (i.e. the original Amershan Pharmacia Co.)

Chromatographic media: SP Sepharose 4 Fast Flow (GE Healthcare Co.)

Column Volume: 5.5 cm×20 cm
Buffer: 20 mM phosphate buffer pH 8.0, 20 mM DTT
20 mM phosphate buffer pH 8.0, 20 mM DTT, 2M NaCl
Flow Rate: 25 mL/min
Detector Wavelength: 280 nm
Sample: about 70% pure HPV33N9C-L1 protein solution, as filtered through a filter membrane with an aperture of 0.22 μm in Example 2.

Elution protocol: eluting undesired proteins with 400 mM NaCl, eluting the protein of interest with 800 mM NaCl, collecting eluate eluted with 800 mM NaCl.

Purification of HPV33N9C-L1 by CHT-II Chromatography (Hydroxyapatite Chromatography)

Equipment: AKTA Explorer 100 preparative liquid chromatography system produced by GE Healthcare (i.e. the original Amershan Pharmacia Co.)

Chromatographic media: CHT-II (purchased from Bio-Rad)

Column Volume: 5.5 cm×20 cm
Buffer: 20 mM phosphate buffer pH8.0, 20 mM DTT,
20 mM phosphate buffer pH 8.0, 20 mM DTT, 2M NaCl
Flow Rate: 20 mL/min
Detector Wavelength: 280 nm
Sample: 800 mM NaCl elution product obtained in the previous step, wherein the NaCl concentration was diluted to 0.5 M.

Elution protocol: eluting undesired proteins with 500 mM NaCl, eluting the protein of interest with 1000 mM NaCl, collecting eluate eluted with 1000 mM NaCl.

Purification of HPV33N9C-L1 by HIC (Hydrophobic Interaction Chromatography)

Equipment: AKTA Explorer 100 preparative liquid chromatography system produced by GE Healthcare (i.e. the original Amershan Pharmacia Co.)

Chromatographic media: Butyl Sepharose 4 Fast Flow (GE Healthcare Co.)

Column Volume: 5.5 cm×20 cm
Buffer: 20 mM phosphate buffer pH8.0, 20 mM DTT,
20 mM phosphate buffer pH 8.0, 20 mM DTT, 2M NaCl
Flow Rate: 20 mL/min
Detector Wavelength: 280 nm
Sample: 1000 mM NaCl elution product obtained in the previous step.

Elution protocol: eluting undesired proteins with 1000 mM NaCl, eluting the protein of interest with 200 mM NaCl, collecting eluate eluted with 200 mM NaCl.

Figure 2:
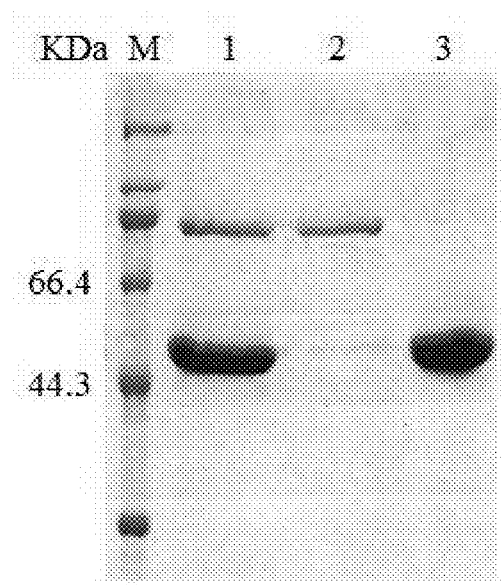
FIG. 2 shows the SDS-PAGE result of HPV33N9C-L1 purified by HIC (Hydrophobic Interaction Chromatography) in Example 3. Lane M: protein molecular weight marker; Lane 1: a sample before purification by using Butyl Sepharose 4 Fast Flow column; Lane 2: a fraction passing the Butyl Sepharose 4 Fast Flow column; Lane 3: a fraction (10 μl) eluted from the Butyl Sepharose 4 Fast Flow column using 200 mmol/L NaCl. The result showed that HPV33N9C-L1 protein purified by Butyl Sepharose 4 Fast Flow column reached a purity of above 98% (see Lane 3).

30 μL 6× loading buffer was added to 150 μL eluate eluted with 200 mM NaCl, and then the resulted solution was mixed homogeneously. After incubating the solution in a water bath at 80° C. for 10 min, a 10 μL sample was subjected to 10% SDS-PAGE at 120V for 120 min. The electrophoretic bands were stained by Coomassie brilliant blue. The electrophoretic result was shown in FIG. 2. The result showed that after said purification step, HPV33N9C-L1 protein had a purity of greater than 98%.

Example 4

Assembly of HPV33N9C-L1 VLPs

Equipment: CENTRASETTE 5 Tangential Flow Filter (Pall Co.), wherein the membrane retention molecular weight was 30 kDa. Sample: HPV33N9C-L1 with a purity of greater than 98% obtained in Example 3.

Sample Renaturation: Sample buffer was exchanged with renaturation buffer (50 mM PB (sodium phosphate buffer) pH 6.0, 2 mM $CaCl_2$, 2 mM $MgCl_2$, 0.5M NaCl, 0.003% Tween-80) thoroughly. The exchange volume was above 10 times of the original volume of the sample. The Tangential Flow Filter was run at a pressure of 0.5 psi and a tangential flow rate of 10 mL/min. When the exchange with renaturation buffer was finished, the renaturation buffer was exchanged with storage buffer (20 mM PB (sodium phosphate buffer) pH 6.5, 0.5M NaCl). The exchange volume was above 4 times of the volume of the sample. The Tangential Flow Filter was run at a pressure of 0.5 psi and a tangential flow rate of 25 mL/min. When the exchange was finished, the sample was aseptically filtrated with a Pall filter (0.20 μm), and thereby obtaining HPV33N9C-L1 VLPs. The HPV33N9C-L1 VLPs were stored at 4° C. for further use.

Example 5

Determination of the Morphology and Immunogenicity of HPV33N9C-L1 VLPs

Transmission Electron Microscopy (TEM) of HPV33N9C-L1 VLPs

Figure 3:
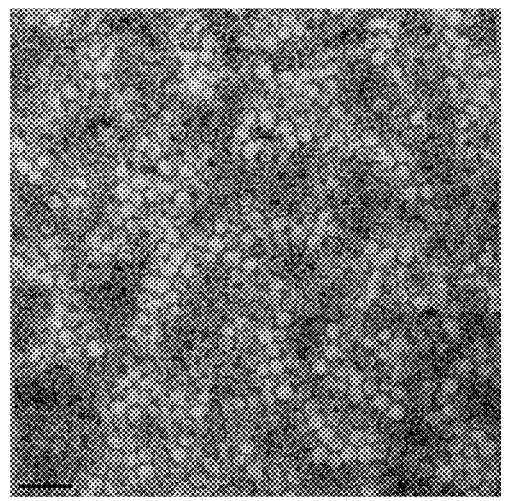
FIG. 3 shows the transmission electron microscopy (TEM) photograph of HPV33N9C-L1 VLPs obtained in Example 4 (taken at 50,000× magnification, Bar=0.2 μm). A large number of VLPs with a radius of about 25 nm were observed in visual field, wherein the particle size was consistent with the theoretic size and the particles were homogenous.

The equipment was a JEOL 100 kV Transmission Electron Microscope (100,000× magnification). HPV33N9C-L1 VLPs obtained in Example 4 were negatively stained with 2% phosphotungstic acid at pH 7.0, and fixed on a copper grid for observation. Results were shown in FIG. 3. A large number of VLPs with a radius of approximately 25 nm, which were homogenous and in a hollow form, were observed.

Dynamic Light-Scattering Measurement of HPV33N9C-L1 VLPs

Figure 4:
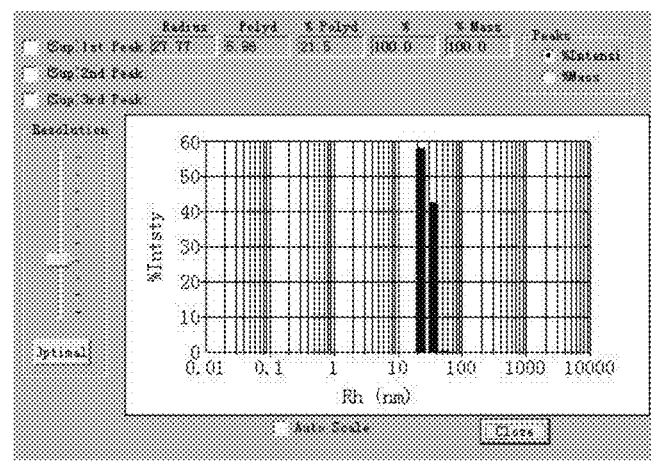
FIG. 4 shows the dynamic light-scattering measurement result of HPV33N9C-L1 VLPs obtained in Example 4. The result showed that HPV33N9C-L1 VLPs had a hydrodynamic radius of 27.77 nm and a particle assembly rate of 100%.

DynaPro MS/X dynamic light-scattering instrument (including a temperature controller) (US Protein Solutions Co.) was used for light-scattering measurements. The Regulation algorithm was used in the measurements. The sample was the HPV33N9C-L1 VLPs obtained in Example 4. The sample was passed through a 0.22 μm filter membrane prior to the measurement. The result was shown in FIG. 4. The result showed that HPV33N9C-L1 VLPs had a hydrodynamic radius of 27.77 nm.

Establishment of a Cellular Model for HPV33 Pseudovirion Neutralization

HPV can hardly be cultured in vitro, and the HPV host is strongly specific. Thus, HPV can hardly be propagated in hosts other than human. That is, there was not an appropriate animal model for HPV. Therefore, in order to evaluate the immune protection of HPV vaccines quickly, it is urgent to establish an effective model for in vitro neutralization assays.

In Vitro Model of Pseudovirion Infection: by means of the characteristic that HPV VLP can package nucleic acids non-specifically, HPV pseudovirion was formed by expressing HPV L1 and L2 protein in cells, and by packaging episomal viral DNA or reporter plasmids introduced heterologously (Yeager, M. D, Aste-Amezaga, M. et al (2000) Virology (278) 570-7). The concrete methods include methods of recombinant viral expression systems and methods of co-transfection of multi-plasmids. Methods of co-transfection of multi-plasmids were used in the Example exemplarily.

Construction of HPV Pseudovirion:

Plasmid p33L1h (the pAAV vector carrying the nucleotide sequence encoding HPV33 L1 protein (NCBI database, P06416.1)), plasmid p33L2h (the pAAV vector carrying the nucleotide sequence encoding HPV33 L2 protein (NCBI database, P06418.1)), and plasmid pN31-EGFP carrying green fluorescent protein gene, were purified by CsCl density gradient centrifugation, wherein said pN31-EGFP and said pAAV vectors were donated by Professor John T. Schiller of NIH. Methods for purifying plasmids using CsCl density gradient centrifugation were well known in the art (see The Molecular Cloning Experiment Guide, 3rd edition).

293FT cells (Invitrogen) cultured on a 10 cm cell culture plate were co-transfected with the purified p33L1h, p33L2h and pN31-EGFP (40 μg for each) by calcium phosphate transfection method. Calcium phosphate transfection method was well known in the art (see The Molecular Cloning Experiment Guide, 3rd edition). In brief, p33L1h, p33L2h and pN31-EGFP (40 μg for each) were added to the mixture of 1 mL HEPES solution (125 μL 1M HEPES pH7.3 per 50 mL deionized water, stored at 4° C.) and 1 mL 0.5M $CaCl_2$ solution. After mixing homogeneously, 2 mL 2× HeBS solution (0.28M NaCl (16.36 g), 0.05M HEPES (11.9 g), and 1.5 mM $Na_2HPO_4$ (0.213 g), dissolved in 1000 mL deionized water, pH 6.96, stored at −70° C.) was added dropwise. After standing at room temperature for 1 min, the mixture was added to the 10 cm cell culture plate where the 293FT cells were cultured. After culturing for 6 hr, the original culture medium was decanted and 10 ml fresh complete medium (Invitrogen Co.) was added. After transfection for 48 hours, the medium was decanted and the cells were washed twice with PBS. Then, the cells were collected and counted. Every $10^8$ cells were re-suspended in 1 mL lysis solution (0.25% Brij58, 9.5 mM $MgCl_2$). After lysing, cell lysate was centrifuged at 5,000 g for 10 min and the supernatant was collected. The Pseudovirion solution was obtained after adding 5M NaCl to a final concentration of 850 mM, and then was stored in small packages at −20° C.

Determination of the Neutralization Titers of Antibodies

293FT cells (Invitrogen) were plated on a 96-well cell culture plate ($1.5 \times 10^4$ cells/well). Neutralization assay was performed five hours later. Serum samples comprising antibodies to be tested were serially diluted with 10% DMEM half-by-half. The diluted samples (50 μL for each) were respectively mixed with 50 μL Pseudovirion solution diluted in 10% DMEM as prepared above (moi=0.1). After incubating at 4° C. for 1 h, the mixture was added to the 96-well cell culture plate coated with 293FT cells. The mixture was then incubated for 72 h at 37° C. Antibody titers of samples were estimated by observing fluorescence. Infection percentage of cells in each well was then checked by flow cytometry (EPICS XL, American Beckman Coulter Co.). The exact antibody titers of serums were calculated. Infection percentage was the percentage of cells in the positive region of the cell sample to be tested minus that in the positive region of the uninfected control cell sample.

Infection-inhibition percentage=(1−infection percentage of wells with serum/infection percentage of wells without serum)× 100%

Neutralization titer of antibodies was defined as the highest dilution fold under which the infection-inhibition percentage reached above 50%. Antibodies were considered as having neutralizing capacity if their infection-inhibition percentage was above 50% after 50 times dilution.

Evaluation of Immune Protection of Vaccination of Animals with HPV33 VLPs

Mice were used to evaluate the immune protection of the HPV33 VLPs according to the invention. Animals for vaccination were 8 BALB/c mice (SPF grade), 4-5 weeks old. HPV33N9C-L1 VLPs were prepared by the methods in Examples 1-4. The particles were diluted to a concentration of 0.1 mg/ml, and then were mixed with equal volume of complete Freund's Adjuvant for the first vaccination, or with equal volume of incomplete Freund's Adjuvant for the booster. The vaccination procedure was as followed: the first vaccination at Week 0, and the booster at Weeks 2, 4 and 6, respectively. Rabbits were vaccinated via muscle injection, with 10 μg per mouse for the first vaccination, and with 10 μg per mouse for the booster.

Figure 5:
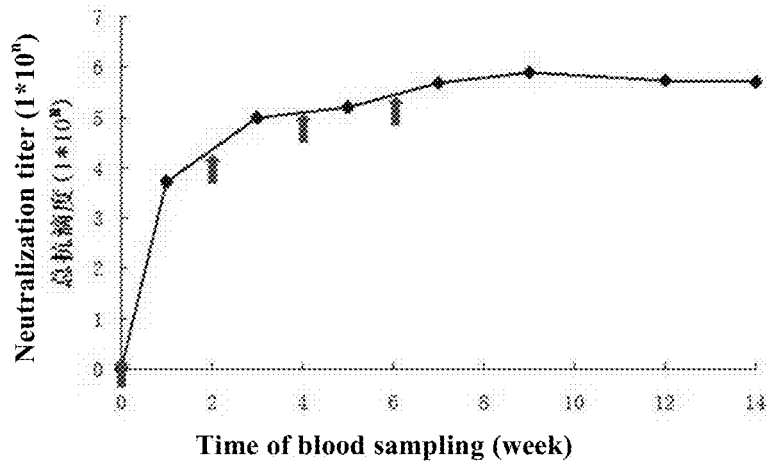
FIG. 5 shows neutralization titers of antibodies in serum at different stages after vaccination of mice with HPV33N9C-L1 VLPs as determined in Example 5. The neutralization titers of antibodies increased significantly two weeks after the first vaccination, and reached a peak level of $10^5$ after a booster.

After the first vaccination, peripheral venous blood was collected every two weeks, and serum was separated. The neutralization titers of antibodies against HPV33 pseudovirion in the mouse serum were determined by the method above. The result was shown in FIG. 5. The result showed HPV33N9C-L1 VLPs obtained by the methods as described in Examples 1-4 had good immunogenicity, could induce the generalization of neutralization antibodies against HPV33 with a high titer in mice, and could be used as an effective vaccine for the prevention of HPV33 infection. In addition to Freund's Adjuvant, other adjuvants well known in the art might also be used in the vaccines, for example, aluminum hydroxide or aluminum phosphate adjuvants.

Rabbits were also used to evaluate the immune protection of the HPV33 VLPs according to the invention. Animals for vaccination were 4 female rabbits (general grade), 6-8 weeks old, purchased from the Disease Prevention and Control Center of Guangxi province. HPV33N9C-L1 VLPs prepared in Examples 1-4 was diluted to a concentration of 0.1 mg/ml, were mixed with equal volume of complete Freund's Adjuvant for the first vaccination, or with equal volume of incomplete Freund's Adjuvant for the booster. The vaccination procedure was as followed: the first vaccination at Week 0, and the booster at Weeks 4, 8 and 12, respectively. Rabbits were vaccinated via muscle injection, with 1.0 mg per rabbit for the first vaccination, and with 1.0 mg per rabbit for the booster.

Figure 6:
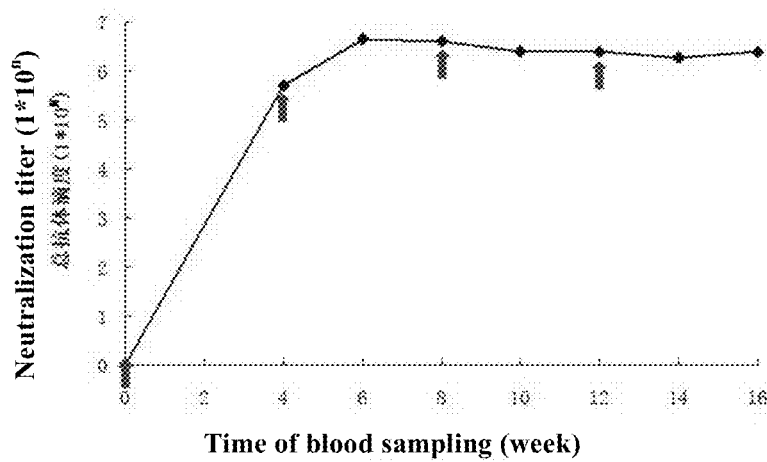
FIG. 6 shows neutralization titers of antibodies in serum at different stages after vaccination of rabbits with HPV33N9C-L1 VLPs as determined in Example 5. The neutralization titers of antibodies increased significantly one month after the first vaccination, and reached a peak level of $10^6$ after a booster.

After the first vaccination, peripheral venous blood was collected every 2 weeks, and serum was separated. The neutralization titers of antibodies against HPV33 pseudovirion in the rabbit serum were determined by the method above. The result was shown in FIG. 6. The result showed that HPV33N9C-L1 VLPs obtained by the methods as described in Examples 1-4 had good immunogenicity, could induce the generalization of neutralization antibodies against HPV33 with a high titer in rabbits, and could be used as an effective vaccine for the prevention of HPV33 infection. In addition to Freund's Adjuvant, other adjuvants well known in the art might also be used in the vaccines, for example, aluminum hydroxide or aluminum phosphate adjuvants.

The results above showed that HPV33 VLPs obtained by the methods of the invention had good immunogenicity, could induce the generalization of neutralization antibodies with a high titer in rabbits, and could be used as an effective vaccine for the prevention of HPV infection.

Example 6

Figure 7:
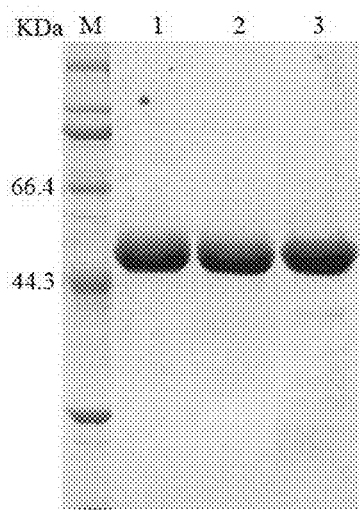
FIG. 7 shows the SDS-PAGE results of the HPV33 L1 proteins having 11, 14 or 19 amino acids truncated at the N-terminal, respectively, i.e. HPV33N11C-L1, HPV33N14C-L1, HPV33N19C-L1 (their amino acid sequences were set forth in SEQ ID NOs: 5, 6 and 7, respectively), as obtained in Example 6. Lane M: protein molecular weight marker; Lane 1: HPV33N11C-L1 protein (the loading volume was 10 μL); Lane 2: HPV33N14C-L1 protein (the loading volume was 10 μL); Lane 3: HPV33N19C-L1 protein (the loading volume was 10 μL). The results showed that the truncated proteins, i.e. HPV33N11C-L1, HPV33N14C-L1, HPV33N19C-L1, as obtained in Example 6, reached a purity of above 98%.

Preparation and Morphologic Observation of HPV33N11C-L1, HPV33N14C-L1, and HPV33N19C-L1 Proteins and VPLs HPV33 L1 proteins having 11, 14 or 19 amino acids truncated at the N-terminal (their amino acid sequences were set forth in SEQ ID NOs: 5, 6 and 7, and their nucleotide sequences were set forth in SEQ ID NOs: 9, 10, and 11, respectively), were prepared and purified basically by the methods as described in Examples 1-3. The three proteins thus obtained had a purity of above 98% (see FIG. 7).

The purified HPV33N11C-L1, HPV33N14C-L1, and HPV33N19C-L1 proteins were assembled into VLPs basically by the method as described in Example 4, respectively.

Figure 8:
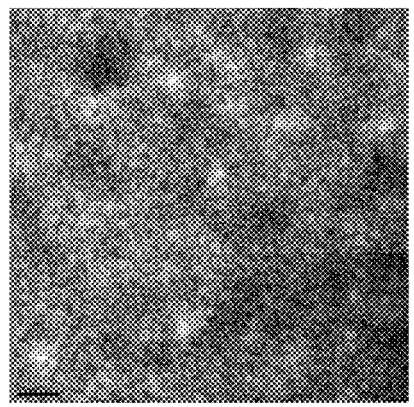
FIG. 8 shows the transmission electron microscopy (TEM) photographs of HPV33N11C-L1 VLPs obtained in Example 6 (taken at 50,000× magnification, Bar=0.2 μm). The result showed that a large number of VLPs with a radius of about 25 nm were observed in visual field, wherein the particle size was consistent with the theoretic size and the particles were homogenous.
Figure 9:
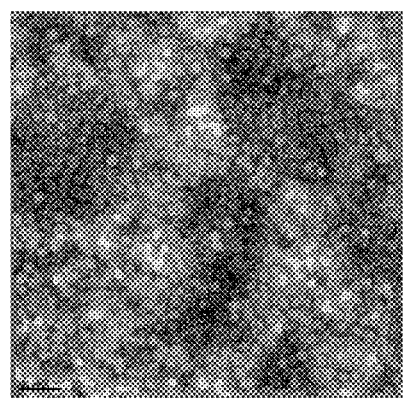
FIG. 9 shows the transmission electron microscopy (TEM) photographs of HPV33N14C-L1 VLPs obtained in Example 6 (taken at 50,000× magnification, Bar=0.2 μm). The result showed that a large number of VLPs with a radius of about 25 nm were observed in visual field, wherein the particle size was consistent with the theoretic size and the particles were homogenous.
Figure 10:
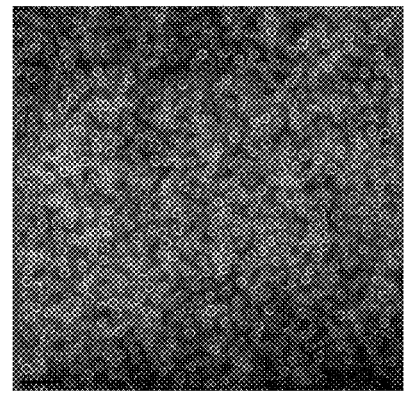
FIG. 10 shows the transmission electron microscopy (TEM) photographs of HPV33N19C-L1 VLPs obtained in Example 6 (taken at 50,000× magnification, Bar=0.2 μm). The result showed that a large number of VLPs with a radius of about 25 nm were observed in visual field, wherein the particle size was consistent with the theoretic size and the particles were homogenous.
Figure 11:
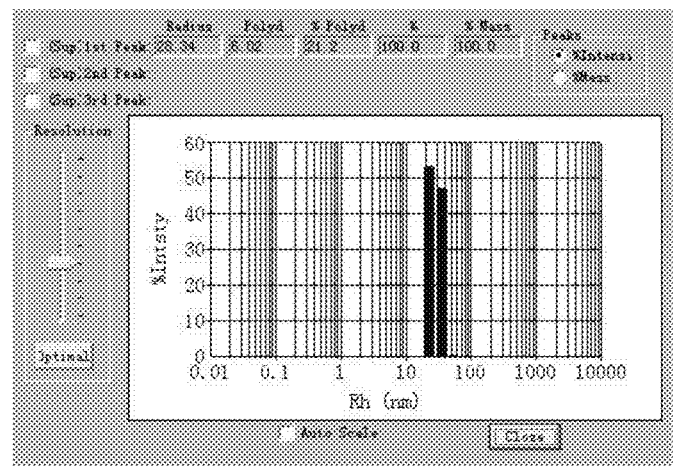
FIG. 11 shows the dynamic light-scattering measurement result of HPV33N11C-L1 VLPs obtained in Example 6. The result showed that HPV33N11C-L1 VLPs had a hydrodynamic radius of 28.34 nm and a particle assembly rate of 100%.
Figure 12:
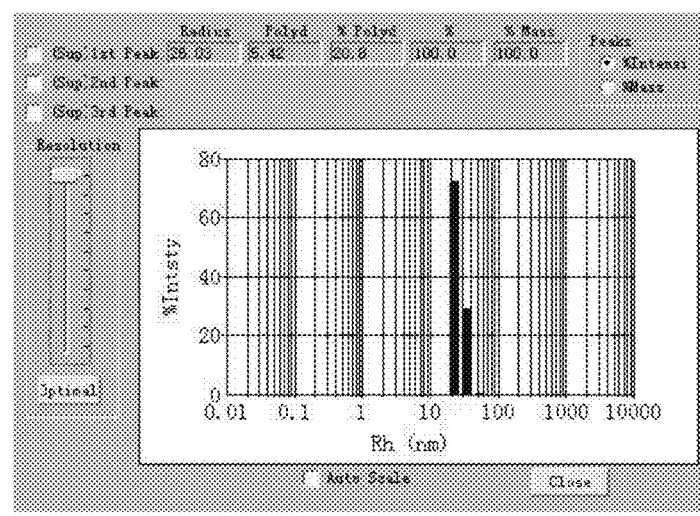
FIG. 12 shows the dynamic light-scattering measurement result of HPV33N14C-L1 VLPs obtained in Example 6. The result showed that HPV33N14C-L1 VLPs had a hydrodynamic radius of 26.03 nm and a particle assembly rate of 100%.
Figure 13:
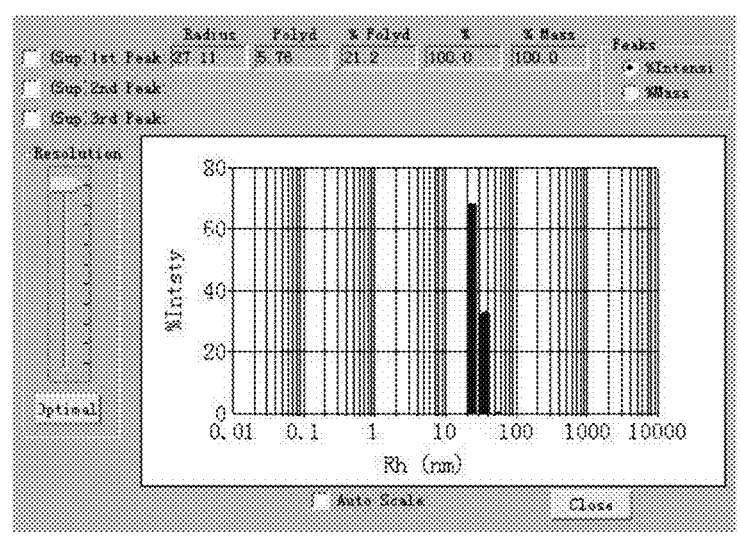
FIG. 13 shows the dynamic light-scattering measurement result of HPV33N19C-L1 VLPs obtained in Example 6. The result showed that HPV33N19C-L1 VLPs had a hydrodynamic radius of 27.11 nm and a particle assembly rate of 100%.

HPV33N11C-L1 VLPs, HPV33N14C-L1 VLPs, and HPV33N19C-L1 VLPs were subjected to transmission electron microscopy and dynamic light scattering observation basically by the method as described in Example 5, respectively. The results were shown in FIGS. 8-13. FIGS. 8, 9 and 10 showed that the truncated proteins could form a large number of VLPs with a radius of about 25 nm, wherein the particle size was consistent with the theoretic size and the particles were homogenous. FIGS. 11, 12 and 13 showed that these VLPs had a hydrodynamic radius of about 27 nm and a particle assembly rate of 100%.

In addition, it was demonstrated by the method as described in Example 5 that the HPV33N11C-L1, HPV33N14C-L1, and HPV33N19C-L1 VLPs obtained in the invention also had good immunogenicity, could induce the generalization of neutralization antibodies with a high titer in animals, and therefore could be used as an effective vaccine for the prevention of HPV infection.

Although the specific embodiments of the present invention have been described in details, those skilled in the art would understand that, according to the teachings disclosed in the specification, various modifications and changes can be made without departing from the sprit or scope of the present invention as generally described, and that such modifications and changes are within the scope of the present invention. The scope of the present invention is given by the appended claims and any equivalents thereof.

The invention claimed is:

1. A truncated HPV33 L1 protein, wherein said truncated HPV33 L1 protein has an amino acid sequence as set forth in SEQ ID NO: 4, SEQ ID NO: 5, SEQ ID NO: 6, or SEQ ID NO: 7.

2. An isolated nucleic acid, encoding the truncated HPV33 L1 protein according to claim 1.

3. A vector comprising the isolated nucleic acid according to claim 2.

4. An isolated host cell comprising the isolated nucleic acid according to claim 2, or a vector comprising the isolated nucleic acid.

5. A HPV33 virus-like particle, comprising or consisting of the truncated HPV33 L1 protein according to claim 1.

6. A composition comprising the truncated HPV33 L1 protein according to claim 1, or an isolated nucleic acid encoding the truncated HPV33 L1 protein, or a vector comprising an isolated nucleic acid encoding the truncated HPV33 L1 protein.

7. A pharmaceutical composition or vaccine comprising the HPV33 virus-like particle according to claim 5, and optionally, a pharmaceutically acceptable carrier, excipient or combination thereof.

8. A method for obtaining a truncated HPV33 L1 protein, comprising expressing the truncated HPV33 L1 protein of claim 1 with an *E. coli* expression system, and carrying out a purification treatment on the lysed supernatant containing said protein.

9. A method for preparing a vaccine, comprising blending the HPV33 virus-like particle according to claim 5 with a pharmaceutically acceptable carrier, excipient or combination thereof.

10. A method for inhibiting HPV33 infection or preventing a disease caused by HPV33 infection, comprising administering to a subject a prophylactically effective amount of the HPV33 virus-like particle according to claim 5 or a pharmaceutical composition or vaccine comprising the HPV33 virus-like particle and, optionally, pharmaceutically acceptable carriers and/or excipients.

11. A truncated HPV33 L1 protein according to claim 1, wherein said truncated HPV33 L1 protein has an amino acid sequence as set forth in SEQ ID NO: 4.

12. A composition comprising the host cell according to claim 4.

13. A composition comprising the HPV33 virus-like particle according to claim 5.

14. A pharmaceutical composition or vaccine according to claim 7, wherein the HPV33 virus-like particle is present in an amount effective for inhibiting HPV33 infection or preventing cervical cancer caused by HPV33 infection.

15. A method for obtaining a truncated HPV33 L1 protein according to claim 8, wherein the method comprises the steps of:
   a) expressing the truncated protein in E. coli;
   b) disrupting the E. coli, which has expressed the truncated protein, in a solution with a salt concentration of 100 mM to 600 mM, and isolating the supernatant;
   c) decreasing the salt concentration of the supernatant obtained in step b) to 100 mM or less by using water or a solution at a low salt concentration, and collecting a precipitate; and
   d) re-dissolving the precipitate obtained in step c) in a solution with a salt concentration of 150 mM to 2500 mM and adding a reductant to the solution, and then isolating the resultant solution, wherein the resultant solution contains the truncated HPV33 L1 protein with a purity of at least 50%.

16. A method for preparing a HPV33 virus-like particle comprising or consisting of a truncated HPV33 L1 protein, wherein said truncated HPV33 L1 protein has an amino acid sequence as set forth in SEQ ID NO: 4, SEQ ID NO: 5, SEQ ID NO: 6, or SEQ ID NO: 7, the method comprising the steps of:
   a) purifying the truncated HPV33 L1 protein as obtained by the method of claim 15 through a chromatography; and
   b) removing the reductant from the truncated protein obtained in step a).

17. A method for inhibiting HPV33 infection or preventing a disease caused by HPV33 infection, comprising administrating to a subject a prophylactically effective amount of the HPV33 virus-like particle obtained by the method according to claim 16.

18. A method for inhibiting HPV33 infection or preventing a disease caused by HPV33 infection, comprising administrating to a subject a prophylactically effective amount of the vaccine obtained by the method according to claim 9.

19. A method for inhibiting HPV33 infection or preventing a disease caused by HPV33 infection according to claim 10, wherein the disease caused by HPV33 infection is cervical cancer.

* * * * *

SEQUENCE LISTING

<160> NUMBER OF SEQ ID NOS: 14

<210> SEQ ID NO 1
<211> LENGTH: 1500
<212> TYPE: DNA
<213> ORGANISM: Human papillomavirus type 33

<400> SEQUENCE: 1
atgtccgtgt ggcggcctag tgaggccaca gtgtacctgc ctcctgtacc tgtatctaaa    60

```
gttgtcagca ctgatgagta tgtgtctcgc acaagcattt attattatgc tggtagttcc      120
agacttcttg ctgttggcca tccatatttt tctattaaaa atcctactaa cgctaaaaaa      180
ttattggtac ccaaagtatc aggcttgcaa tatagggttt ttagggtccg tttaccagat      240
cctaataaat ttggatttcc tgacacctcc ttttataacc ctgatacaca acgattagta      300
tgggcatgtg taggccttga ataggtaga gggcagccat taggcgttgg cataagtggt       360
catcctttat taaacaaatt tgatgacact gaaaccggta acaagtatcc tggacaaccg      420
ggtgctgata tagggaatg tttatccatg gattataaac aaacacagtt atgtttactt       480
ggatgtaagc ctccaacagg ggaacattgg ggtaaaggtg ttgcttgtac taatgcagca      540
cctgccaatg attgtccacc tttagaactt ataaatacta ttattgagga tggtgatatg      600
gtggacacag gatttggttg catggatttt aaaacattgc aggctaataa agtgatgtt       660 cctattgata tttgtggcag tacatgcaaa tatccagatt atttaaaaat gactagtgag      720
ccttatggtg atagtttatt tttctttctt cgacgtgaac aaatgtttgt aagcactttt      780
tttaataggg ctggtaaatt aggagaggct gttcccgatg acctgtacat taaaggttca      840
ggaactactg cctctattca aagcagtgct ttttttccca ctcctagtgg atcaatggtt      900
acttccgaat ctcagttatt taataagcca tattggctac aacgtgcaca aggtcataat      960
aatggtattt gttggggcaa tcaggtattt gttactgtgg tagataccac tcgcagtact     1020
aatatgactt tatgcacaca ggtaactagt gacagtacat ataaaaatga aaattttaaa     1080
gaatatataa gacatgttga agaatatgat ctacagtttg tttttcaact atgcaaagtt     1140
accttaactg cagaagttat gacatatatt catgctatga atccagatat tttagaagat     1200
tggcaatttg gtttaacacc tcctccatct gctagtttac aggatcccta taggtttgtt     1260
acctctcagg ctattacgtg tcaaaaaaca gtacctccaa aggaaaagga agacccctta     1320
ggtaaataca cattttggga agtggattta aaggaaaaat tttcagcaga tttagatcag     1380
tttcctttgg gacgcaagtt tttattacag gcaggtctta agcaaaaacc taaacttaaa     1440
cgtgcagccc ccacatccac ccgcacatca tctgcaaaac gcaaaaaggt taaaaaataa     1500
```

<210> SEQ ID NO 2
<211> LENGTH: 1500
<212> TYPE: DNA
<213> ORGANISM: Human papillomavirus type 33

<400> SEQUENCE: 2

```
atgtccgtgt ggcggcctag tgaggccaca gtgtacctgc ctcctgtacc tgtatctaaa       60
gttgtcagca ctgatgagta tgtgtctcgc acaagcattt attattatgc tggtagttcc      120
agacttcttg ctgttggcca tccatatttt tctattaaaa atcctactaa cgctaaaaaa      180
ttattggtac ccaaagtatc aggcttgcaa tatagggttt ttagggtccg tttaccagat      240
cctaataaat ttggatttcc tgacacctcc ttttataacc ctgatacaca acgattagta      300
tgggcatgtg taggccttga ataggtaga gggcagccat taggcgttgg cataagtggt       360
catcctttat taaacaaatt tgatgacact gaaaccagta acaagtatcc tggacaaccg      420
ggtgctgata tagggaatg tttatccatg gattataaac aaacacagtt atgtttactt       480
ggatgtaagc ctccaacagg ggaacattgg ggtaaaggtg ttgcttgtac taatgcagca      540
cctgccaatg attgtccacc tttagaactt ataaatacta ttattgagga tggtgatatg      600
gtggacacag gatttggttg catggatttt aaaacattgc aggctaataa agtgatgtt       660
```

```
cctattgata tttgtggcag tacatgcaaa tatccagatt atttaaaaat gactagtgag      720
ccttatggtg atagtttatt tttctttctt cgacgtgaac aaatgtttgt aagcactttt      780
tttaataggg ctggtacatt aggagaggct gttcccgatg acctgtacat taaaggttca     840
ggaactactg cctctattca aagcagtgct ttttttccca ctcctagtgg atcaatggtt     900
acttccgaat ctcagttatt taataagcca tattggctac aacgtgcaca aggtcataat     960
aatggtattt gttggggcaa tcaggtattt gttactgtgg tagataccac tcgcagtact    1020
aatatgactt tatgcacaca ggtaactagt gacagtacat ataaaaatga aaattttaaa    1080
gaatatatat gacatgttga agaatatgat ctacagtttg ttttcaact atgcaaagtt     1140 accttaactg cagaagttat gacatatatt catgctatga atccagatat tttagaagat    1200
tggcaatttg gtttaacacc tcctccatct gctagtttac aggataccta taggtttgtt    1260
acctctcagg ctattacgtg tcaaaaaaca gtacctccaa aggaaaagga agacccctta    1320
ggtaaataca cattttggga agtggattta aaggaaaaat tttcagcaga tttagatcag    1380
tttcctttgg gacgcaagtt tttattacag gcaggtctta aagcaaaacc taaacttaaa    1440
cgtgcagccc ccacatccac ccgcacatca tctgcaaaac gcaaaaaggt taaaaaataa    1500

<210> SEQ ID NO 3
<211> LENGTH: 1500
<212> TYPE: DNA
<213> ORGANISM: Human papillomavirus type 33

<400> SEQUENCE: 3
atgtccgtgt ggcggcctag tgaggccaca gtgtacctgc ctcctgtacc tgtatctaaa      60
gttgtcagca ctgatgagta tgtgtctcgc acaagcattt attattatgc tggtagttcc     120
agacttcttg ctgttggcca tccatatttt tctattaaaa atcctactaa cgctaaaaaa     180
ttattggtac ccaaagtatc aggcttgcaa tatagggttt tagggtccg tttaccagat     240 cctaataaat ttggatttcc tgacacctcc ttttataacc ctgatacaca acgattagta     300
tgggcatgtg taggccttga aataggtaga gggcagccat taggcgttgg cataagtggt     360
catcctttat taaacaaatt tgatgacact gaaaccggta acaagtatcc tggacaaccg     420
ggtgctgata ataggaaatg tttatccatg gattataaac aaacacagtt atgtttactt     480
ggatgtaagc ctccaacagg ggaacattgg ggtaaaggtg ttgcttgtac taatgcagca     540
cctgccaatg attgtccacc tttagaactt ataaatacta ttattgagga tggtgatatg     600
gtggacacag gatttggttg catggatttt aaaacattgc aggctaataa agtgatgtt      660 cctattgata tttgtggcag tacatgcaaa tatccagatt atttaaaaat gactagtgag     720
ccttatggtg atagtttatt tttctttctt cgacgtgaac aaatgtttgt aagcactttt     780
tttaataggg ctggtacatt aggagaggct gttcccgatg acctgtacat taaaggttca     840
ggaactactg cctctattca aagcagtgct ttttttccca ctcctagtgg atcaatggtt     900
acttccgaat ctcagttatt taataagcca tattggctac aacgtgcaca aggtcataat     960
aatggtattt gttggggcaa tcaggtattt gttactgtgg tagataccac tcgcagtact    1020
aatatgactt tatgcacaca ggtaactagt gacagtacat ataaaaatga aaattttaaa    1080
gaatatatat gacatgttga agaatatgat ctacagtttg ttttcaact atgcaaagtt     1140 accttaactg cagaagttat gacatatatt catgctatga atccagatat tttagaagat    1200
tggcaatttg gtttaacacc tcctccatct gctagtttac aggataccta taggtttgtt    1260
acctctcagg ctattacgtg tcaaaaaaca gtacctccaa aggaaaagga agacccctta    1320
```

-continued

```
ggtaaataca catttttggga agtggattta aaggaaaaat tttcagcaga tttagatcag    1380
ttccttttgg gacgcaagtt tttattacag gcaggtctta aagcaaaacc taaacttaaa    1440
cgtgcagccc ccacatccac ccgcacatca tctgcaaaac gcaaaaggt taaaaataa    1500
```

<210> SEQ ID NO 4
<211> LENGTH: 491
<212> TYPE: PRT
<213> ORGANISM: Artificial
<220> FEATURE:
<223> OTHER INFORMATION: Truncated L1 protein of HPV33

<400> SEQUENCE: 4

```
Met Thr Val Tyr Leu Pro Pro Val Pro Val Ser Lys Val Val Ser Thr
1               5                   10                  15

Asp Glu Tyr Val Ser Arg Thr Ser Ile Tyr Tyr Ala Gly Ser Ser
            20                  25                  30

Arg Leu Leu Ala Val Gly His Pro Tyr Phe Ser Ile Lys Asn Pro Thr
        35                  40                  45

Asn Ala Lys Lys Leu Leu Val Pro Lys Val Ser Gly Leu Gln Tyr Arg
    50                  55                  60

Val Phe Arg Val Arg Leu Pro Asp Pro Asn Lys Phe Gly Phe Pro Asp
65                  70                  75                  80

Thr Ser Phe Tyr Asn Pro Asp Thr Gln Arg Leu Val Trp Ala Cys Val
                85                  90                  95

Gly Leu Glu Ile Gly Arg Gly Gln Pro Leu Gly Val Gly Ile Ser Gly
            100                 105                 110

His Pro Leu Leu Asn Lys Phe Asp Asp Thr Glu Thr Gly Asn Lys Tyr
        115                 120                 125

Pro Gly Gln Pro Gly Ala Asp Asn Arg Glu Cys Leu Ser Met Asp Tyr
    130                 135                 140

Lys Gln Thr Gln Leu Cys Leu Leu Gly Cys Lys Pro Pro Thr Gly Glu
145                 150                 155                 160

His Trp Gly Lys Gly Val Ala Cys Thr Asn Ala Ala Pro Ala Asn Asp
                165                 170                 175

Cys Pro Pro Leu Glu Leu Ile Asn Thr Ile Ile Glu Asp Gly Asp Met
            180                 185                 190

Val Asp Thr Gly Phe Gly Cys Met Asp Phe Lys Thr Leu Gln Ala Asn
        195                 200                 205

Lys Ser Asp Val Pro Ile Asp Ile Cys Gly Ser Thr Cys Lys Tyr Pro
    210                 215                 220

Asp Tyr Leu Lys Met Thr Ser Glu Pro Tyr Gly Asp Ser Leu Phe Phe
225                 230                 235                 240

Phe Leu Arg Arg Glu Gln Met Phe Val Arg His Phe Phe Asn Arg Ala
                245                 250                 255

Gly Lys Leu Gly Glu Ala Val Pro Asp Asp Leu Tyr Ile Lys Gly Ser
            260                 265                 270

Gly Thr Thr Ala Ser Ile Gln Ser Ser Ala Phe Phe Pro Thr Pro Ser
        275                 280                 285

Gly Ser Met Val Thr Ser Glu Ser Gln Leu Phe Asn Lys Pro Tyr Trp
    290                 295                 300

Leu Gln Arg Ala Gln Gly His Asn Asn Gly Ile Cys Trp Gly Asn Gln
305                 310                 315                 320

Val Phe Val Thr Val Val Asp Thr Thr Arg Ser Thr Asn Met Thr Leu
                325                 330                 335
```

```
Cys Thr Gln Val Thr Ser Asp Ser Thr Tyr Lys Asn Glu Asn Phe Lys
                340                 345                 350

Glu Tyr Ile Arg His Val Glu Tyr Asp Leu Gln Phe Val Phe Gln
            355                 360                 365

Leu Cys Lys Val Thr Leu Thr Ala Glu Val Met Thr Tyr Ile His Ala
370                 375                 380

Met Asn Pro Asp Ile Leu Glu Asp Trp Gln Phe Gly Leu Thr Pro Pro
385                 390                 395                 400

Pro Ser Ala Ser Leu Gln Asp Thr Tyr Arg Phe Val Thr Ser Gln Ala
                405                 410                 415

Ile Thr Cys Gln Lys Thr Val Pro Pro Lys Glu Lys Glu Asp Pro Leu
            420                 425                 430

Gly Lys Tyr Thr Phe Trp Glu Val Asp Leu Lys Glu Lys Phe Ser Ala
                435                 440                 445

Asp Leu Asp Gln Phe Pro Leu Gly Arg Lys Phe Leu Leu Gln Ala Gly
            450                 455                 460

Leu Lys Ala Lys Pro Lys Leu Lys Arg Ala Ala Pro Thr Ser Thr Arg
465                 470                 475                 480

Thr Ser Ser Ala Lys Arg Lys Val Lys Lys
                485                 490

<210> SEQ ID NO 5
<211> LENGTH: 489
<212> TYPE: PRT
<213> ORGANISM: Artificial
<220> FEATURE:
<223> OTHER INFORMATION: Truncated L1 protein of HPV33

<400> SEQUENCE: 5

Met Tyr Leu Pro Pro Val Pro Val Ser Lys Val Val Ser Thr Asp Glu
1               5                   10                  15

Tyr Val Ser Arg Thr Ser Ile Tyr Tyr Tyr Ala Gly Ser Ser Arg Leu
            20                  25                  30

Leu Ala Val Gly His Pro Tyr Phe Ser Ile Lys Asn Pro Thr Asn Ala
        35                  40                  45

Lys Lys Leu Leu Val Pro Lys Val Ser Gly Leu Gln Tyr Arg Val Phe
50                  55                  60

Arg Val Arg Leu Pro Asp Pro Asn Lys Phe Gly Phe Pro Asp Thr Ser
65                  70                  75                  80

Phe Tyr Asn Pro Asp Thr Gln Arg Leu Val Trp Ala Cys Val Gly Leu
                85                  90                  95

Glu Ile Gly Arg Gly Gln Pro Leu Gly Val Gly Ile Ser Gly His Pro
            100                 105                 110

Leu Leu Asn Lys Phe Asp Asp Thr Glu Thr Gly Asn Lys Tyr Pro Gly
        115                 120                 125

Gln Pro Gly Ala Asp Asn Arg Glu Cys Leu Ser Met Asp Tyr Lys Gln
130                 135                 140

Thr Gln Leu Cys Leu Leu Gly Cys Lys Pro Pro Thr Gly Glu His Trp
145                 150                 155                 160

Gly Lys Gly Val Ala Cys Thr Asn Ala Ala Pro Ala Asn Asp Cys Pro
                165                 170                 175

Pro Leu Glu Leu Ile Asn Thr Ile Ile Glu Asp Gly Asp Met Val Asp
            180                 185                 190

Thr Gly Phe Gly Cys Met Asp Phe Lys Thr Leu Gln Ala Asn Lys Ser
        195                 200                 205
```

Asp Val Pro Ile Asp Ile Cys Gly Ser Thr Cys Lys Tyr Pro Asp Tyr
210                 215                 220

Leu Lys Met Thr Ser Glu Pro Tyr Gly Asp Ser Leu Phe Phe Phe Leu
225                 230                 235                 240

Arg Arg Glu Gln Met Phe Val Arg His Phe Asn Arg Ala Gly Lys
            245                 250                 255

Leu Gly Glu Ala Val Pro Asp Asp Leu Tyr Ile Lys Gly Ser Gly Thr
            260                 265                 270

Thr Ala Ser Ile Gln Ser Ser Ala Phe Phe Pro Thr Pro Ser Gly Ser
        275                 280                 285

Met Val Thr Ser Glu Ser Gln Leu Phe Asn Lys Pro Tyr Trp Leu Gln
        290                 295                 300

Arg Ala Gln Gly His Asn Asn Gly Ile Cys Trp Gly Asn Gln Val Phe
305                 310                 315                 320

Val Thr Val Val Asp Thr Thr Arg Ser Thr Asn Met Thr Leu Cys Thr
                325                 330                 335

Gln Val Thr Ser Asp Ser Thr Tyr Lys Asn Glu Asn Phe Lys Glu Tyr
                340                 345                 350

Ile Arg His Val Glu Glu Tyr Asp Leu Gln Phe Val Phe Gln Leu Cys
            355                 360                 365

Lys Val Thr Leu Thr Ala Glu Val Met Thr Tyr Ile His Ala Met Asn
370                 375                 380

Pro Asp Ile Leu Glu Asp Trp Gln Phe Gly Leu Thr Pro Pro Pro Ser
385                 390                 395                 400

Ala Ser Leu Gln Asp Thr Tyr Arg Phe Val Thr Ser Gln Ala Ile Thr
                405                 410                 415

Cys Gln Lys Thr Val Pro Pro Lys Glu Lys Glu Asp Pro Leu Gly Lys
            420                 425                 430

Tyr Thr Phe Trp Glu Val Asp Leu Lys Glu Lys Phe Ser Ala Asp Leu
            435                 440                 445

Asp Gln Phe Pro Leu Gly Arg Lys Phe Leu Leu Gln Ala Gly Leu Lys
        450                 455                 460

Ala Lys Pro Lys Leu Lys Arg Ala Ala Pro Thr Ser Thr Arg Thr Ser
465                 470                 475                 480

Ser Ala Lys Arg Lys Lys Val Lys Lys
                485

<210> SEQ ID NO 6
<211> LENGTH: 486
<212> TYPE: PRT
<213> ORGANISM: Artificial
<220> FEATURE:
<223> OTHER INFORMATION: Truncated L1 protein of HPV33

<400> SEQUENCE: 6

Met Pro Val Pro Val Ser Lys Val Val Ser Thr Asp Glu Tyr Val Ser
1               5                   10                  15

Arg Thr Ser Ile Tyr Tyr Tyr Ala Gly Ser Ser Arg Leu Leu Ala Val
            20                  25                  30

Gly His Pro Tyr Phe Ser Ile Lys Asn Pro Thr Asn Ala Lys Lys Leu
        35                  40                  45

Leu Val Pro Lys Val Ser Gly Leu Gln Tyr Arg Val Phe Arg Val Arg
    50                  55                  60

Leu Pro Asp Pro Asn Lys Phe Gly Phe Pro Asp Thr Ser Phe Tyr Asn
65                  70                  75                  80

```
Pro Asp Thr Gln Arg Leu Val Trp Ala Cys Val Gly Leu Glu Ile Gly
                85                  90                  95

Arg Gly Gln Pro Leu Gly Val Gly Ile Ser Gly His Pro Leu Leu Asn
            100                 105                 110

Lys Phe Asp Asp Thr Glu Thr Gly Asn Lys Tyr Pro Gly Gln Pro Gly
        115                 120                 125

Ala Asp Asn Arg Glu Cys Leu Ser Met Asp Tyr Lys Gln Thr Gln Leu
    130                 135                 140

Cys Leu Leu Gly Cys Lys Pro Pro Thr Gly Glu His Trp Gly Lys Gly
145                 150                 155                 160

Val Ala Cys Thr Asn Ala Ala Pro Ala Asn Asp Cys Pro Pro Leu Glu
                165                 170                 175

Leu Ile Asn Thr Ile Ile Glu Asp Gly Asp Met Val Asp Thr Gly Phe
            180                 185                 190

Gly Cys Met Asp Phe Lys Thr Leu Gln Ala Asn Lys Ser Asp Val Pro
        195                 200                 205

Ile Asp Ile Cys Gly Ser Thr Cys Lys Tyr Pro Asp Tyr Leu Lys Met
    210                 215                 220

Thr Ser Glu Pro Tyr Gly Asp Ser Leu Phe Phe Phe Leu Arg Arg Glu
225                 230                 235                 240

Gln Met Phe Val Arg His Phe Phe Asn Arg Ala Gly Lys Leu Gly Glu
                245                 250                 255

Ala Val Pro Asp Asp Leu Tyr Ile Lys Gly Ser Gly Thr Thr Ala Ser
            260                 265                 270

Ile Gln Ser Ser Ala Phe Phe Pro Thr Pro Ser Gly Ser Met Val Thr
        275                 280                 285

Ser Glu Ser Gln Leu Phe Asn Lys Pro Tyr Trp Leu Gln Arg Ala Gln
    290                 295                 300

Gly His Asn Asn Gly Ile Cys Trp Gly Asn Gln Val Phe Val Thr Val
305                 310                 315                 320

Val Asp Thr Thr Arg Ser Thr Asn Met Thr Leu Cys Thr Gln Val Thr
                325                 330                 335

Ser Asp Ser Thr Tyr Lys Asn Glu Asn Phe Lys Glu Tyr Ile Arg His
            340                 345                 350

Val Glu Glu Tyr Asp Leu Gln Phe Val Phe Gln Leu Cys Lys Val Thr
        355                 360                 365

Leu Thr Ala Glu Val Met Thr Tyr Ile His Ala Met Asn Pro Asp Ile
    370                 375                 380

Leu Glu Asp Trp Gln Phe Gly Leu Thr Pro Pro Pro Ser Ala Ser Leu
385                 390                 395                 400

Gln Asp Thr Tyr Arg Phe Val Thr Ser Gln Ala Ile Thr Cys Gln Lys
                405                 410                 415

Thr Val Pro Pro Lys Glu Lys Glu Asp Pro Leu Gly Lys Tyr Thr Phe
            420                 425                 430

Trp Glu Val Asp Leu Lys Glu Lys Phe Ser Ala Asp Leu Asp Gln Phe
        435                 440                 445

Pro Leu Gly Arg Lys Phe Leu Leu Gln Ala Gly Leu Lys Ala Lys Pro
    450                 455                 460

Lys Leu Lys Arg Ala Ala Pro Thr Ser Thr Arg Thr Ser Ser Ala Lys
465                 470                 475                 480

Arg Lys Lys Val Lys Lys
                485
```

```
<210> SEQ ID NO 7
<211> LENGTH: 481
<212> TYPE: PRT
<213> ORGANISM: Artificial
<220> FEATURE:
<223> OTHER INFORMATION: Truncated L1 protein of HPV33

<400> SEQUENCE: 7
```

| Met | Lys | Val | Val | Ser | Thr | Asp | Glu | Tyr | Val | Ser | Arg | Thr | Ser | Ile | Tyr |
|---|---|---|---|---|---|---|---|---|---|---|---|---|---|---|---|
| 1 | | | | 5 | | | | | 10 | | | | | 15 | |

| Tyr | Tyr | Ala | Gly | Ser | Ser | Arg | Leu | Leu | Ala | Val | Gly | His | Pro | Tyr | Phe |
|---|---|---|---|---|---|---|---|---|---|---|---|---|---|---|---|
| | | | 20 | | | | | 25 | | | | | 30 | | |

| Ser | Ile | Lys | Asn | Pro | Thr | Asn | Ala | Lys | Lys | Leu | Leu | Val | Pro | Lys | Val |
|---|---|---|---|---|---|---|---|---|---|---|---|---|---|---|---|
| | | 35 | | | | | 40 | | | | | 45 | | | |

| Ser | Gly | Leu | Gln | Tyr | Arg | Val | Phe | Arg | Val | Arg | Leu | Pro | Asp | Pro | Asn |
|---|---|---|---|---|---|---|---|---|---|---|---|---|---|---|---|
| | 50 | | | | | 55 | | | | | 60 | | | | |

| Lys | Phe | Gly | Phe | Pro | Asp | Thr | Ser | Phe | Tyr | Asn | Pro | Asp | Thr | Gln | Arg |
|---|---|---|---|---|---|---|---|---|---|---|---|---|---|---|---|
| 65 | | | | | 70 | | | | | 75 | | | | | 80 |

| Leu | Val | Trp | Ala | Cys | Val | Gly | Leu | Glu | Ile | Gly | Arg | Gly | Gln | Pro | Leu |
|---|---|---|---|---|---|---|---|---|---|---|---|---|---|---|---|
| | | | | 85 | | | | | 90 | | | | | 95 | |

| Gly | Val | Gly | Ile | Ser | Gly | His | Pro | Leu | Leu | Asn | Lys | Phe | Asp | Asp | Thr |
|---|---|---|---|---|---|---|---|---|---|---|---|---|---|---|---|
| | | | 100 | | | | | 105 | | | | | 110 | | |

| Glu | Thr | Gly | Asn | Lys | Tyr | Pro | Gly | Gln | Pro | Gly | Ala | Asp | Asn | Arg | Glu |
|---|---|---|---|---|---|---|---|---|---|---|---|---|---|---|---|
| | | 115 | | | | | 120 | | | | | 125 | | | |

| Cys | Leu | Ser | Met | Asp | Tyr | Lys | Gln | Thr | Gln | Leu | Cys | Leu | Leu | Gly | Cys |
|---|---|---|---|---|---|---|---|---|---|---|---|---|---|---|---|
| | 130 | | | | | 135 | | | | | 140 | | | | |

| Lys | Pro | Pro | Thr | Gly | Glu | His | Trp | Gly | Lys | Gly | Val | Ala | Cys | Thr | Asn |
|---|---|---|---|---|---|---|---|---|---|---|---|---|---|---|---|
| 145 | | | | | 150 | | | | | 155 | | | | | 160 |

| Ala | Ala | Pro | Ala | Asn | Asp | Cys | Pro | Pro | Leu | Glu | Leu | Ile | Asn | Thr | Ile |
|---|---|---|---|---|---|---|---|---|---|---|---|---|---|---|---|
| | | | | 165 | | | | | 170 | | | | | 175 | |

| Ile | Glu | Asp | Gly | Asp | Met | Val | Asp | Thr | Gly | Phe | Gly | Cys | Met | Asp | Phe |
|---|---|---|---|---|---|---|---|---|---|---|---|---|---|---|---|
| | | | 180 | | | | | 185 | | | | | 190 | | |

| Lys | Thr | Leu | Gln | Ala | Asn | Lys | Ser | Asp | Val | Pro | Ile | Asp | Ile | Cys | Gly |
|---|---|---|---|---|---|---|---|---|---|---|---|---|---|---|---|
| | | 195 | | | | | 200 | | | | | 205 | | | |

| Ser | Thr | Cys | Lys | Tyr | Pro | Asp | Tyr | Leu | Lys | Met | Thr | Ser | Glu | Pro | Tyr |
|---|---|---|---|---|---|---|---|---|---|---|---|---|---|---|---|
| | 210 | | | | | 215 | | | | | 220 | | | | |

| Gly | Asp | Ser | Leu | Phe | Phe | Phe | Leu | Arg | Arg | Glu | Gln | Met | Phe | Val | Arg |
|---|---|---|---|---|---|---|---|---|---|---|---|---|---|---|---|
| 225 | | | | | 230 | | | | | 235 | | | | | 240 |

| His | Phe | Phe | Asn | Arg | Ala | Gly | Lys | Leu | Gly | Glu | Ala | Val | Pro | Asp | Asp |
|---|---|---|---|---|---|---|---|---|---|---|---|---|---|---|---|
| | | | | 245 | | | | | 250 | | | | | 255 | |

| Leu | Tyr | Ile | Lys | Gly | Ser | Gly | Thr | Thr | Ala | Ser | Ile | Gln | Ser | Ser | Ala |
|---|---|---|---|---|---|---|---|---|---|---|---|---|---|---|---|
| | | | 260 | | | | | 265 | | | | | 270 | | |

| Phe | Phe | Pro | Thr | Pro | Ser | Gly | Ser | Met | Val | Thr | Ser | Glu | Ser | Gln | Leu |
|---|---|---|---|---|---|---|---|---|---|---|---|---|---|---|---|
| | | 275 | | | | | 280 | | | | | 285 | | | |

| Phe | Asn | Lys | Pro | Tyr | Trp | Leu | Gln | Arg | Ala | Gln | Gly | His | Asn | Asn | Gly |
|---|---|---|---|---|---|---|---|---|---|---|---|---|---|---|---|
| | 290 | | | | | 295 | | | | | 300 | | | | |

| Ile | Cys | Trp | Gly | Asn | Gln | Val | Phe | Val | Thr | Val | Val | Asp | Thr | Thr | Arg |
|---|---|---|---|---|---|---|---|---|---|---|---|---|---|---|---|
| 305 | | | | | 310 | | | | | 315 | | | | | 320 |

| Ser | Thr | Asn | Met | Thr | Leu | Cys | Thr | Gln | Val | Thr | Ser | Asp | Ser | Thr | Tyr |
|---|---|---|---|---|---|---|---|---|---|---|---|---|---|---|---|
| | | | | 325 | | | | | 330 | | | | | 335 | |

| Lys | Asn | Glu | Asn | Phe | Lys | Glu | Tyr | Ile | Arg | His | Val | Glu | Glu | Tyr | Asp |
|---|---|---|---|---|---|---|---|---|---|---|---|---|---|---|---|
| | | | 340 | | | | | 345 | | | | | 350 | | |

| Leu | Gln | Phe | Val | Phe | Gln | Leu | Cys | Lys | Val | Thr | Leu | Thr | Ala | Glu | Val |
|---|---|---|---|---|---|---|---|---|---|---|---|---|---|---|---|
| | | 355 | | | | | 360 | | | | | 365 | | | |

```
Met Thr Tyr Ile His Ala Met Asn Pro Asp Ile Leu Glu Asp Trp Gln
            370                 375                 380

Phe Gly Leu Thr Pro Pro Ser Ala Ser Leu Gln Asp Thr Tyr Arg
385                 390                 395                 400

Phe Val Thr Ser Gln Ala Ile Thr Cys Gln Lys Thr Val Pro Pro Lys
                    405                 410                 415

Glu Lys Glu Asp Pro Leu Gly Lys Tyr Thr Phe Trp Glu Val Asp Leu
                420                 425                 430

Lys Glu Lys Phe Ser Ala Asp Leu Asp Gln Phe Pro Leu Gly Arg Lys
            435                 440                 445

Phe Leu Leu Gln Ala Gly Leu Lys Ala Lys Pro Lys Leu Lys Arg Ala
450                 455                 460

Ala Pro Thr Ser Thr Arg Thr Ser Ser Ala Lys Arg Lys Lys Val Lys
465                 470                 475                 480

Lys

<210> SEQ ID NO 8
<211> LENGTH: 1476
<212> TYPE: DNA
<213> ORGANISM: Artificial
<220> FEATURE:
<223> OTHER INFORMATION: Truncated L1 gene of HPV33

<400> SEQUENCE: 8
```

| | | | | | |
|---|---|---|---|---|---|
| atgacagtgt | acctgcctcc | tgtacctgta | tctaaagttg | tcagcactga | tgagtatgtg | 60 |
| tctcgcacaa | gcatttatta | ttatgctggt | agttccagac | ttcttgctgt | tggccatcca | 120 |
| tattttctta | ttaaaaatcc | tactaacgct | aaaaaattat | tggtacccaa | agtatcaggc | 180 |
| ttgcaatata | gggttttag | ggtccgttta | ccagatccta | taaaatttgg | atttcctgac | 240 |
| acctcctttt | ataaccctga | tacacaacga | ttagtatggg | catgtgtagg | ccttgaaata | 300 |
| ggtagagggc | agccattagg | cgttggcata | agtggtcatc | ctttattaaa | caaatttgat | 360 |
| gacactgaaa | ccggtaacaa | gtatcctgga | caaccgggtg | ctgataatag | ggaatgttta | 420 |
| tccatggatt | ataaacaaac | acagttatgt | ttacttggat | gtaagcctcc | aacaggggaa | 480 |
| cattggggta | aaggtgttgc | ttgtactaat | gcagcacctg | ccaatgattg | tccaccttta | 540 |
| gaacttataa | atactattat | tgaggatggt | gatatggtgg | acacaggatt | tggttgcatg | 600 |
| gattttaaaa | cattgcaggc | taataaaagt | gatgttccta | ttgatatttg | tggcagtaca | 660 |
| tgcaaatatc | cagattattt | aaaaatgact | agtgagcctt | atggtgatag | tttattttc | 720 |
| tttcttcgac | gtgaacaaat | gtttgtaaga | cacttttta | ataggctgg | taaattagga | 780 |
| gaggctgttc | ccgatgacct | gtacattaaa | ggttcaggaa | ctactgcctc | tattcaaagc | 840 |
| agtgcttttt | ttcccactcc | tagtggatca | atggttactt | ccgaatctca | gttatttaat | 900 |
| aagccatatt | ggctacaacg | tgcacaaggt | cataataatg | gtatttgttg | gggcaatcag | 960 |
| gtatttgtta | ctgtggtaga | taccactcgc | agtactaata | tgactttatg | cacacaggta | 1020 |
| actagtgaca | gtacatataa | aaatgaaaat | tttaaagaat | atataagaca | tgttgaagaa | 1080 |
| tatgatctac | agtttgtttt | tcaactatgc | aaagttacct | taactgcaga | agttatgaca | 1140 |
| tatattcatg | ctatgaatcc | agatattta | gaagattggc | aatttggttt | aacacctcct | 1200 |
| ccatctgcta | gtttacagga | taccttaagg | tttgttacct | ctcaggctat | acgtgtcaa | 1260 |
| aaaacagtac | ctccaaagga | aaaggaagac | cccttaggta | aatacacatt | tgggaagtg | 1320 |
| gatttaaagg | aaaaatttc | agcagattta | gatcagtttc | ctttgggacg | caagttttta | 1380 |

| | |
|---|---|
| ttacaggcag gtcttaaagc aaaacctaaa cttaaacgtg cagcccccac atccacccgc | 1440 |
| acatcatctg caaaacgcaa aaaggttaaa aaataa | 1476 |

<210> SEQ ID NO 9
<211> LENGTH: 1470
<212> TYPE: DNA
<213> ORGANISM: Artificial
<220> FEATURE:
<223> OTHER INFORMATION: Truncated L1 gene of HPV33

<400> SEQUENCE: 9

| | |
|---|---|
| atgtacctgc ctcctgtacc tgtatctaaa gttgtcagca ctgatgagta tgtgtctcgc | 60 |
| acaagcattt attattatgc tggtagttcc agacttcttg ctgttggcca tccatatttt | 120 |
| tctattaaaa atcctactaa cgctaaaaaa ttattggtac ccaaagtatc aggcttgcaa | 180 |
| tatagggttt ttagggtccg tttaccagat cctaataaat ttggatttcc tgacacctcc | 240 |
| ttttataacc ctgatacaca acgattagta tgggcatgtg taggccttga aataggtaga | 300 |
| gggcagccat taggcgttgg cataagtggt catcctttat taaacaaatt tgatgacact | 360 |
| gaaaccggta acaagtatcc tggacaaccg ggtgctgata tagggaatg tttatccatg | 420 |
| gattataaac aaacacagtt atgtttactt ggatgtaagc ctccaacagg gaacattgg | 480 |
| ggtaaaggtg ttgcttgtac taatgcagca cctgccaatg attgtccacc tttagaactt | 540 |
| ataaatacta ttattgagga tggtgatatg gtggacacag gatttggttg catggatttt | 600 |
| aaaacattgc aggctaataa aagtgatgtt cctattgata tttgtggcag tacatgcaaa | 660 |
| tatccagatt atttaaaaat gactagtgag cctattggtg ataagtttat tttcttctct tctt | 720 |
| cgacgtgaac aaatgtttgt aagacacttt tttaataggg ctggtaaatt aggagaggct | 780 |
| gttcccgatg acctgtacat taaaggttca ggaactactg cctctattca aagcagtgct | 840 |
| ttttttccca ctcctagtgg atcaatggtt acttccgaat ctcagttatt taataagcca | 900 |
| tattggctac aacgtgcaca aggtcataat aatggtattt gttggggcaa tcaggtattt | 960 |
| gttactgtgg tagataccac tcgcagtact aatatgactt tatgcacaca ggtaactagt | 1020 |
| gacagtacat ataaaaatga aaattttaaa gaatatatatata gacatgttga agaatatgat | 1080 |
| ctacagtttg tttttcaact atgcaaagtt accttaactg cagaagttat gacatatatt | 1140 |
| catgctatga atccagatat tttagaagat tggcaatttg gtttaacacc tcctccatct | 1200 |
| gctagtttac aggataccta taggtttgtt acctctcagg ctattacgtg tcaaaaaaca | 1260 |
| gtacctccaa aggaaaagga agacccctta ggtaaataca catttttggga agtggattta | 1320 |
| aaggaaaaat tttcagcaga tttagatcag tttcctttgg gacgcaagtt tttattacag | 1380 |
| gcaggtctta agcaaaaacc taacttaaa cgtgcagccc ccacatccac ccgcacatca | 1440 |
| tctgcaaaac gcaaaaaggt taaaaaataa | 1470 |

<210> SEQ ID NO 10
<211> LENGTH: 1461
<212> TYPE: DNA
<213> ORGANISM: Artificial
<220> FEATURE:
<223> OTHER INFORMATION: Truncated L1 gene of HPV33

<400> SEQUENCE: 10

| | |
|---|---|
| atgcctgtac ctgtatctaa agttgtcagc actgatgagt atgtgtctcg cacaagcatt | 60 |
| tattattatg ctggtagttc cagacttctt gctgttggcc atccatattt ttctattaaa | 120 |
| aatcctacta acgctaaaaa attattggta cccaaagtat caggcttgca atatagggtt | 180 |

```
tttagggtcc gtttaccaga tcctaataaa tttggatttc ctgacacctc cttttataac    240
cctgatacac aacgattagt atgggcatgt gtaggccttg aaataggtag agggcagcca    300
ttaggcgttg gcataagtgg tcatccttta ttaaacaaat ttgatgacac tgaaaccggt    360
aacaagtatc ctggacaacc gggtgctgat aatagggaat gtttatccat ggattataaa    420
caaacacagt tatgtttact tggatgtaag cctccaacag gggaacattg gggtaaaggt    480
gttgcttgta ctaatgcagc acctgccaat gattgtccac ctttagaact tataaatact    540
attattgagg atggtgatat ggtggacaca ggatttggtt gcatggattt taaaacattg    600
caggctaata aaagtgatgt tcctattgat atttgtggca gtacatgcaa atatccagat    660
tatttaaaaa tgactagtga gccttatggt gatagtttat ttttctttct tcgacgtgaa    720
caaatgtttg taagacactt ttttaatagg ctggtaaaat taggagaggc tgttcccgat    780
gacctgtaca ttaaaggttc aggaactact gcctctattc aaagcagtgc ttttttttccc    840 actcctagtg gatcaatggt tacttccgaa tctcagttat ttaataagcc atattggcta    900
caacgtgcac aaggtcataa taatggtatt tgttgggggca atcaggtatt tgttactgtg    960
gtagatacca ctcgcagtac taatatgact ttatgcacac aggtaactag tgacagtaca   1020
tataaaaatg aaaattttaa agaatatata agacatgttg aagaatatga tctacagttt   1080
gtttttcaac tatgcaaagt taccttaact gcagaagtta tgacatatat tcatgctatg   1140
aatccagata ttttagaaga ttggcaattt ggtttaacac ctcctccatc tgctagttta   1200
caggatacct ataggtttgt tacctctcag gctattacgt gtcaaaaaac agtacctcca   1260
aaggaaaagg aagacccctt aggtaaatac acattttggg aagtggattt aaaggaaaaa   1320
ttttcagcag atttagatca gtttcctttg ggacgcaagt ttttattaca ggcaggtctt   1380
aaagcaaaac ctaaacttaa acgtgcagcc cccacatcca cccgcacatc atctgcaaaa   1440
cgcaaaaagg ttaaaaaata a                                              1461
```

<210> SEQ ID NO 11
<211> LENGTH: 1446
<212> TYPE: DNA
<213> ORGANISM: Artificial
<220> FEATURE:
<223> OTHER INFORMATION: Truncated L1 gene of HPV33

<400> SEQUENCE: 11

```
atgaaagttg tcagcactga tgagtatgtg tctcgcacaa gcatttatta ttatgctggt     60
agttccagac ttcttgctgt tggccatcca tattttttcta ttaaaaatcc tactaacgct    120
aaaaaattat tggtacccaa agtatcaggc ttgcaatata gggtttttag ggtccgttta    180
ccagatccta taaatttggg atttcctgac acctcctttt ataaccctga tacacaacga    240
ttagtatggg catgtgtagg ccttgaaata ggtagagggc agccattagg cgttggcata    300
agtggtcatc ctttattaaa caaatttgat gacactgaaa ccggtaacaa gtatcctgga    360
caaccgggtg ctgataatag ggaatgttta tccatggatt ataaacaaac acagttatgt    420
ttacttggat gtaagcctcc aacaggggaa cattgggggta aggtgttgc ttgtactaat    480 gcagcacctg ccaatgattg tccacctttaa gaacttataaa atactattat tgaggatggt    540
gatatggtgg acacaggatt tggttgcatg gattttaaaa cattgcaggc taataaaagt    600
gatgttccta ttgatatttg tggcagtaca tgcaaatatc cagattattt aaaaaatgact    660 agtgagcctt atggtgatag tttatttttc tttcttcgac gtgaacaaat gtttgtaaga    720
```

```
cacttttta  atagggctgg  taaattagga  gaggctgttc  ccgatgacct  gtacattaaa    780
ggttcaggaa  ctactgcctc  tattcaaagc  agtgcttttt  ttcccactcc  tagtggatca    840
atggttactt  ccgaatctca  gttatttaat  aagccatatt  ggctacaacg  tgcacaaggt    900
cataataatg  gtatttgttg  gggcaatcag  gtatttgtta  ctgtggtaga  taccactcgc    960
agtactaata  tgactttatg  cacacaggta  actagtgaca  gtacatataa  aaatgaaaat   1020
tttaaagaat  atataagaca  tgttgaagaa  tatgatctac  agtttgtttt  tcaactatgc   1080
aaagttacct  taactgcaga  agttatgaca  tatattcatg  ctatgaatcc  agatatttta   1140
gaagattggc  aatttggttt  aacacctcct  ccatctgcta  gtttacagga  tacctatagg   1200
tttgttacct  ctcaggctat  tacgtgtcaa  aaaacagtac  ctccaaagga  aaaggaagac   1260
cccttaggta  aatacacatt  tgggaagtg  gatttaaagg  aaaaattttc  agcagattta   1320
gatcagtttc  ctttgggacg  caagttttta  ttacaggcag  gtcttaaagc  aaaacctaaa   1380
cttaaacgtg  cagcccccac  atccacccgc  acatcatctg  caaaacgcaa  aaaggttaaa   1440
aaataa                                                                   1446

<210> SEQ ID NO 12
<211> LENGTH: 23
<212> TYPE: DNA
<213> ORGANISM: Artificial
<220> FEATURE:
<223> OTHER INFORMATION: Primer

<400> SEQUENCE: 12
catatgtccg tgtggcggcc tag                                                  23

<210> SEQ ID NO 13
<211> LENGTH: 26
<212> TYPE: DNA
<213> ORGANISM: Artificial
<220> FEATURE:
<223> OTHER INFORMATION: Primer

<400> SEQUENCE: 13
gtcgacttat tttttaacct ttttgc                                               26

<210> SEQ ID NO 14
<211> LENGTH: 24
<212> TYPE: DNA
<213> ORGANISM: Artificial
<220> FEATURE:
<223> OTHER INFORMATION: Primer

<400> SEQUENCE: 14
catatgacag tgtacctgcc tcct                                                 24
```